(12) United States Patent
Bell et al.

(10) Patent No.: US 8,106,077 B2
(45) Date of Patent: Jan. 31, 2012

(54) COMPOUNDS AND METHODS FOR MODULATING FXR

(75) Inventors: Michael Gregory Bell, Indianapolis, IN (US); Robert Anthony Doti, Indianapolis, IN (US); Matthew Scott Dowling, Irvine, CA (US); Michael James Genin, Zionsville, IN (US); Peter Ambrose Lander, Indianapolis, IN (US); Tianwei Ma, Carmel, IN (US); Nathan Bryan Mantlo, Brownsburg, IN (US); Jason Matthew Ochoada, Greenwood, IN (US); Lindsay Scott Stelzer, Indianapolis, IN (US); Ryan Edward Stites, Indianapolis, IN (US); Alan M Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 513 days.

(21) Appl. No.: 12/298,769

(22) PCT Filed: May 22, 2007

(86) PCT No.: PCT/US2007/069416
§ 371 (c)(1),
(2), (4) Date: Oct. 28, 2008

(87) PCT Pub. No.: WO2007/140174
PCT Pub. Date: Dec. 6, 2007

(65) Prior Publication Data
US 2009/0093524 A1    Apr. 9, 2009

(51) Int. Cl.
*A61K 31/4192* (2006.01)
*C07D 249/06* (2006.01)

(52) U.S. Cl. ...................................... 514/359; 548/255
(58) Field of Classification Search .................. 548/255; 514/359
See application file for complete search history.

(56) References Cited

U.S. PATENT DOCUMENTS 5,990,139 A    11/1999    Yano et al.

FOREIGN PATENT DOCUMENTS

| WO | WO 03/015771 | 2/2003 |
|---|---|---|
| WO | WO 2004/048349 | 6/2004 |
| WO | WO 2005/065683 | 7/2005 |

*Primary Examiner* — Patricia Morris
(74) *Attorney, Agent, or Firm* — Elizabeth Dingess-Hammond

(57) ABSTRACT

Compounds of formula (I) wherein variables are as defined herein and their pharmaceutical compositions and methods of use are disclosed as useful for treating dyslipidemia and related diseases.

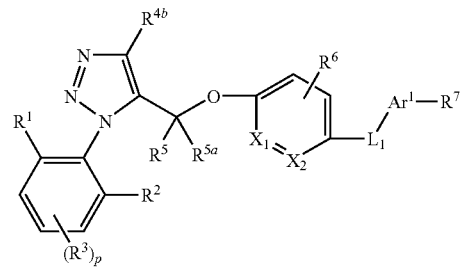

9 Claims, No Drawings

COMPOUNDS AND METHODS FOR MODULATING FXR

This application claims the benefit of U.S. Provisional Application Ser. No. 60/808,104, filed 24 May 2006; U.S. Provisional Application Ser. No. 60/870,001, filed 14 Dec. 2006; and PCT Application Serial No. PCT/US2007/069416, filed 22 May 2007, each hereby incorporated by reference in their entirety.

FIELD OF THE INVENTION

The current invention relates to the fields of medicinal organic chemistry, pharmacology, and medicine. Specifically, the invention relates to novel compounds useful for the treatment of diseases related to dyslipidemia.

BACKGROUND OF THE INVENTION

Dyslipidemia and diseases related to dyslipidemia e.g. atherosclerosis, coronary artery disease, stroke, etc., are major causes of death, morbidity, and economic loss. Plasma lipids, especially cholesterol fractions, are recognized as having a significant role in cardiovascular health. Favorable modulation of plasma lipid such as triglycerides, HDL cholesterol, and LDL cholesterol is desirable.

Numerous efforts are underway to provide safe and efficacious molecular entities for the treatment of diseases related to dyslipidemia. For example, International application WO 2004/048349 A1 discloses compounds useful as farnesoid X receptor (FXR) agonists.

FXR agonists are ligands for a nuclear receptor that regulates the transcription of genes that control triglyceride, cholesterol, and carbohydrate metabolism. The above efforts and others not withstanding, there remains a need to discover and develop compounds that are believed to be (1) potent, (2) efficacious (based on in-vivo models) and/or (3) selective agonists of FXR. Such compounds would be useful for treatment of disorders characterized by or resulting from an undesirable lipid profile including dyslipidemia, atherosclerosis, diabetes and related diseases.

The present invention provides compounds that that are believed to be (1) potent, (2) efficacious (based on in-vivo models) and/or (3) selective agonists of the FXR.

SUMMARY OF THE INVENTION

The present invention provides a compound of formula

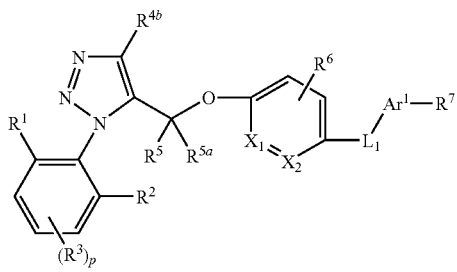

wherein
p is 0, 1 or 2;
$X_1$ is C or N and $X_2$ is C or N; provided that both $X_1$ and $X_2$ are not N;

$R^1$ and $R^2$ are independently selected from the group consisting of hydrogen, $C_1$-$C_3$ alkyl, $C_1$-$C_3$ haloalkyl, $C_1$-$C_3$ thiohaloalkyl, $C_1$-$C_3$ alkoxy, $C_1$-$C_3$ haloalkoxy, and halo;
$R^3$ is independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy, and halo;
$R^{4b}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;
$R^5$ and $R^{5a}$ are independently selected from the group consisting of hydrogen, and $C_1$-$C_3$ alkyl;
$R^6$ is selected from the group consisting of hydrogen, $C_1$-$C_3$ alkyl, $C_1$-$C_3$ haloalkyl, halo, and —$NO_2$;
$L_1$ is selected from the group consisting of a bond, $CR^a$=$CR^b$, ethynyl, $C_1$-$C_3$ alkyl-S—, $C_1$-$C_3$ alkyl-O—, $N(R^c)$—$C_1$-$C_3$ alkyl, and —$C_1$-$C_3$ alkyl-$N(R^c)$—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl, and $C_4$-$C_8$ alkylcycloalkyl;
$Ar^1$ is selected from the group consisting of indolyl, benzothienyl, benzoisothiazolyl, indazolyl, naphthyl, phenyl, pyridinyl, pyrazolyl, pyrrolyl, thienyl, thiazolyl, and furanyl, each optionally substituted with one or two groups independently selected from the group consisting of hydroxy, $C_1$-$C_3$ alkyl, $C_1$-$C_3$ haloalkyl, halo, $C_2$-$C_4$ alkenyl, $C_2$-$C_4$ alkynyl, $C_1$-$C_4$ alkoxy, —$OC_1$-$C_2$ alkylphenyl, and $NHC(O)R^{10}$;
$R^7$ is selected from the group consisting of —COOH, —$C_1$-$C_3$ alkylCOOH, —O—$C_1$-$C_3$ alkylCOOH, —$C_3$-$C_8$ cycloalkylCOOH and, —$CONR^{11}R^{11}$;
each $R^{10}$ is independently selected from the group consisting of hydrogen, $C_1$-$C_3$ alkyl, and phenyl;
each $R^{11}$ is independently hydrogen, or $C_1$-$C_5$ alkyl; or a pharmaceutically acceptable salt thereof.

The compounds of present invention are agonists of FXRs. The compounds of present invention are useful for beneficially altering lipid profiles, including but not limited to lowering total cholesterol, lowering LDL cholesterol, lowering VLDL cholesterol levels, raising HDL levels, lowering triglyceride levels and beneficially sensitizing production of insulin in response to glucose levels. Thus the present invention provides a method for treating FXR mediated conditions such as dyslipidemia and diseases related to dyslipidemia comprising administering a therapeutically effective amount of a compound of present invention to a patient in need thereof.

The present invention also provides a pharmaceutical composition comprising a compound of the present invention and a pharmaceutically acceptable carrier.

The present invention also relates to the use of a compound of the present invention for the manufacture of a medicament.

DETAILED DESCRIPTION OF THE INVENTION

The term "dyslipidemia" as used herein refers to abnormality in, or abnormal amounts of lipids and lipoproteins in the blood and the disease states resulting, caused by, exacerbated by or adjunct to such abnormality (see *Dorland's Illustrated Medical Dictionary, 29th edition*, W.B Saunders publishing Company, New York, N.Y.). Disease states encompassed within the definition of dyslipidemia as used herein include hyperlipidemia, hypertriglyceremia, low plasma HDL, high plasma LDL, high plasmaVLDL, liver cholestasis, and hypercholesterolemia.

The phrase "diseases related to dyslipidemia" as used herein refers to diseases including but not limited to atherosclerosis, thrombosis, coronary artery disease, stroke, and hypertension. Diseases related to dyslipidemia also include metabolic diseases such as obesity, diabetes, insulin resistance, and complications thereof. Complications of diabetes include but are not limited diabetic retinopathy.

As used herein, the term "patient" refers to humans, companion animals (e.g. dogs and cats and the like), and livestock animals.

The terms "treatment" "treat" and "treating" include ameliorating, halting, restraining, slowing, and reversing the progression of, or reducing the severity of pathological symptoms of dyslipidemia and diseases related to dyslipidemia.

As used herein, the term "therapeutically effective amount" means an amount of a compound of the invention that is part of an approved therapeutic regimen, or is determined by a qualified prescriber to be sufficient taken as directed, for treating a condition, or detrimental effects thereof herein described.

The term "pharmaceutically acceptable" is used herein as an adjective and means substantially non-deleterious to the recipient patient.

The term "$C_1$-$C_3$ alkyl" represents a straight or branched hydrocarbon moiety having from 1 to 3 carbon atoms, including methyl, ethyl, n-propyl, and isopropyl. It is understood by one of skill in the art that a "$C_1$-$C_3$ alkyl" is synonymous with a "$C_1$-$C_3$ alkylene" a diradical when the "$C_1$-$C_3$ alkyl" group is sandwiched between two groups such that it is becomes a diradical. Similarly, the terms "$C_1$-$C_4$ alkyl" or "$C_1$-$C_5$ alkyl" or "$C_1$-$C_6$" refer to straight or branched chain alkyl group having 1 to 4 or 1 to 5 or 1 to 6 carbon atoms respectively.

The term "$C_2$-$C_4$ alkenyl" or the like represents a straight or branched hydrocarbon moiety having at least one double bond and having from 2 to 4 carbon atoms. Examples include but are not limited to vinyl, propenyl, 2-butenyl.

The term "$C_2$-$C_4$ alkynyl" or the like represents a straight or branched hydrocarbon moiety having at least one triple bond and having from 2 to 4 carbon atoms. Examples include but are not limited to vinyl, propynyl, 2-butynyl, and the like.

The term "$C_3$-$C_6$ cycloalkyl" refers to a saturated carbocyclic ring having from 3 to 6 carbon atoms (or as indicated), including but not limited to cyclopropyl, cyclopentyl and cyclohexyl. Similarly, the term "$C_3$-$C_8$ cycloalkyl" refers to a saturated carbocyclic ring having from 3 to 8 carbon atoms including but not limited to cyclopropyl, cyclopentyl and cyclohexyl.

The term "$C_4$-$C_5$ alkylcycloalkyl" as used herein refers to the combination of an alkyl and a cycloalkyl group such that the total number of carbon atoms is 4 to 5. For example, $C_4$-$C_5$ alkylcycloalkyl includes —$CH_2$Cyclopropyl, i.e. methylcyclopropyl which is $C_4$alkylcycloalkyl.

The term "halo" means halogens including iodo, chloro, bromo and fluoro.

The term "$C_1$-$C_3$ haloalkyl" refers to a $C_1$-$C_3$ alkyl (or as indicated) group substituted with one, two, three or more halogen atoms as indicated or chemically appropriate. Examples of $C_1$-$C_3$ haloalkyl include but are not limited to trifluoromethyl, chloroethyl, and 2-chloropropyl.

A "$C_1$-$C_3$ alkoxy" group is a $C_1$-$C_3$ alkyl moiety connected through an oxy linkage. Examples of alkoxy groups include but are not limited to methoxy (—OMe (—$OCH_3$)), ethoxy (—OEt (—$OCH_2CH_3$)), propoxy (—OPr (—$OCH_2CH_2CH_3$)), isopropoxy (—OiPr (—$OCHCH_3CH_3$)), etc.

The term "—$C_1$-$C_3$ alkyl-O—" referred to as alkyloxy represents an alkyl group ($C_1$-$C_5$ alkyl or as indicated) terminating in an oxygen atom as distinct from alkoxy (—O—$C_1$-$C_5$ alkyl) reading from left to right. For example radicals or groups such as —$CH_2$O—, —$CH_2CH_2$O—, and —$CH(CH_3)$O— are herein classified as alkyloxy groups.

The term "$C_1$-$C_3$ haloalkoxy" refers to a $C_1$-$C_3$ alkoxy wherein one or more of the hydrogen atoms on the alkyl portion have been replaced with halogens. Examples of $C_1$-$C_3$ haloalkoxy groups include difluoromethoxy, trifluoromethoxy, 2-haloethoxy, 2,2,2-trifluoroethoxy, up to and including like groups having the indicated number of carbon atoms.

It is understood that when $Ar^1$ is bicyclic, attachment of $Ar^1$ to the ring containing $R^6$ can occur at any carbon atom of the bicyclic ring unless otherwise indicated.

A compound of the invention may occur as any one of its isomers all of which are objects of the invention. Certain compounds of the invention may possess one or more chiral centers, and thus, may exist in optically active forms. Likewise, compounds of the invention may have alkenyl groups, and thus, may exist as geometric isomers. All such isomers as well as the mixtures thereof are within the ambit of the present invention. If a particular stereoisomer is desired, it can be prepared by methods well known in the art.

PREFERRED EMBODIMENTS OF THE INVENTION

Preferably $X_1$ and $X_2$ are both C. Also preferred is a compound of the invention wherein $X_1$ is N.

Preferably p is 0, or 1. More preferably, p is 0.

Preferably $R^1$ and $R^2$ group are each independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy, —$SC_1$-$C_3$ alkyl, —$SC_1$-$C_3$ haloalkyl, and halo. More preferably, $R^1$ and $R^2$ groups are independently selected from the group consisting of hydrogen, chloro, fluoro, $CF_3$, $OCF_3$, and $SCF_3$.

A preferred $R^3$ group is selected from the group consisting of hydrogen, $C_1$-$C_3$ alkyl, $C_1$-$C_3$ haloalkyl, $C_1$-$C_3$ alkoxy, $C_1$-$C_3$ haloalkoxy, and halo. More preferred is an $R^3$ group selected from the group consisting of hydrogen, chloro, fluoro, $CF_3$, $OCF_3$, and $SCF_3$. Most preferably, $R^3$ is hydrogen or absent.

Preferably, $R^{4b}$ is independently selected from H, methyl, ethyl, propyl, isopropyl, cyclopropyl, $CF_3$, and methylcyclopropyl. More preferably, $R^{4b}$ is $CF_3$, isopropyl or cyclopropyl.

Preferably, $R^5$ and $R^{5a}$ are each independently selected from the group consisting of hydrogen, methyl and ethyl. More preferably, $R^5$ and $R^{5a}$ are both hydrogen.

A preferred $R^6$ group is selected from the group consisting of hydrogen, halo, $C_1$-$C_3$ alkyl, $C_2$-$C_3$ alkenyl, hydroxy, —$NO_2$, and —$OC_1$-$C_2$ alkyl. More preferably, $R^6$ is selected from the group consisting of hydrogen, halo, methyl, and methoxy. Most preferably, $R^6$ is hydrogen, chloro, or methyl.

Preferred $L_1$ $L_1$ is preferably selected from the group consisting of a bond, CH=CH, ethynyl, —$CH_2$S—, —$C(CH_3)_2$—S—, —$CH(CH_2CH_3)$S—, —$CH(CH_3)$S—, —$CH(CH_3)CH_2$—S—, —$CH(CH_3)CH_2$O—, —$C(CH_3)_2$O—, —$CH(CH_3)$O—, —$CH(CH_2CH_3)$O—, —$N(R^c)(CH_2)_m$—, and —$(CH_2)_m$—$N(R^c)$— wherein $R^c$ is hydrogen or $C_1$-$C_3$ alkyl, m is 1, 2, or 3. More preferably, $L_1$ is a bond, CH=CH, —$N(CH_3)CH_2$, —$N(CH_3)CH_2CH_2$, or —$N(CH_3)CH_2CH_2CH_2$—. More particularly preferred $L_1$ is a bond, —$N(CH_3)CH_2$, or —$N(CH_3)CH_2$. Most preferably $L_1$ is —$N(CH_3)CH_2$, or —$N(CH_3)CH_2CH_2$.

A preferred $Ar^1$ group is selected from the group consisting of optionally substituted indolyl, indazolyl, thienyl, benzothienyl, benzisothiazolyl, phenyl, pyridinyl, pyrrolyl, thiazolyl, and furanyl. More preferably, $Ar^1$ is selected from the group consisting of optionally substituted benzothienyl, indolyl, indazolyl, benzoisothiazolyl, and phenyl. A particularly preferred $Ar^1$ is phenyl, indolyl, benzothienyl, or benzoisothiazolyl. Preferably $Ar^1$ is optionally substituted with one or two groups independently selected from the group consisting of halo, $C_1$-$C_3$ alkyl, $C_1$-$C_3$ alkoxy, $C_1$-$C_3$ haloalkoxy, and $C_1$-$C_3$ haloalkyl.

A preferred $R^7$ substituent is COOH or $CONHR^{11}$. More preferably, $R^7$ is COOH or $CONH_2$, $—CONHCH_3$, or $CONHC_2H_5$. Most preferably $R^7$ is COOH.

$R^{10}$ is preferably hydrogen, or $C_1$-$C_3$ alkyl.

$R^{11}$ is preferably $C_1$-$C_3$ alkyl.

Also preferred is a compound of the invention wherein:
p is 0 or 1;
$X_1$ and $X_2$ are both C, or $X_1$ is N and $X_2$ is C;
$R^1$ and $R^2$ are independently selected from the group consisting of hydrogen, fluoro, chloro, $CF_3$, $SCF_3$, $OCF_3$,
$R^3$ is hydrogen, fluoro, chloro $C_1$-$C_3$ alkyl, $CF_3$, $SCF_3$, or $OCF_3$;
$R^{4b}$ is H, $C_1$-$C_3$ alkyl, $C_1$-$C_3$ haloalkyl, $C_1$-$C_3$ haloalkoxy, or $C_3$-$C_4$ cycloalkyl;
$R^5$ and $R^{5a}$ are each independently selected from H or $C_1$-$C_3$ alkyl;
$Ar^1$ group is phenyl, indolyl, pyridinyl, pyrrolyl, thienyl, naphthyl, thiazolyl, furanyl, pyrazolyl, indazolyl, benzoisothiazolyl, and benzothienyl each optionally substituted with one to two groups independently selected from $C_1$-$C_5$ alkyl, $C_1$-$C_3$ alkoxy, $C_1$-$C_2$ haloalkoxy, and $C_1$-$C_3$ haloalkyl;
$R^6$ is hydrogen, methyl, ethyl or chloro;
$L_1$ is a bond, ethenyl, $—CH(CH_3)—S—$, $C(CH_3)_2—S—$, $—CH_2O—$, $—CH_2CH_2O—$, $—CH(CH_3)—O—$, $—CH(CH_3)CH_2—O—$, $—CH(CH_2CH_3)—O—$, $—CH_2NH—$, $—CH_2CH_2NH—$, $—N(R^c)CH_2—$, $N(R^c)CH_2CH_2—$, or $N(R^c)CH_2CH_2CH_2—$; wherein $R^c$ is hydrogen, $C_1$-$C_2$ alkyl, benzyl or $—CH_2CH_2—O—CH_2—$;
$R^7$ is COOH, $—CH_2COOH$, $—CH(CH_3)COOH$, -cyclopropylCOOH, $—C(CH_3)_2COOH$, $CONH_2$, $C(O)NHCH_3$, or $C(O)NHCH_2CH_3$;
$R^{10}$ is hydrogen or $C_1$-$C_2$ alkyl; and
$R^{11}$ is hydrogen or $C_1$-$C_2$ alkyl.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $R^5$ and $R^{5a}$ are both hydrogen; $L_1$ is ethenyl, acetylene, $—N(CH_3)CH_2—$, or $—N(CH_3)CH_2CH_2—$; $R^6$ is hydrogen, methyl, chloro or bromo; $Ar^1$ is phenyl, indolyl, indazolyl, benzothienyl, or benzoisothiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is $—N(CH_3)CH_2—$, or $—N(CH_3)CH_2CH_2—$; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is $—N(CH_3)CH_2—$, or $—N(CH_3)CH_2CH_2—$; $R^5$ and $R^{5a}$ are both hydrogen; $R^6$ is hydrogen, methyl, ethyl or chloro; $Ar^1$ is phenyl, optionally substituted with a group independently selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is a bond, $—N(CH_3)CH_2—$, or $—N(CH_3)CH_2CH_2—$; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl, $—N(CH_3)CH_2—$, or $—N(CH_3)CH_2CH_2—$; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is a bond, $—CH(CH_3)O$, $—CH(CH_3)CH_2O$, $—CH(CH_3)S$, $—C(CH_3)_2S$, $—CH_2—NH—$, and $—CH_2N(CH_3)—$; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl, $—CH(CH_3)O$, $—CH(CH_3)CH_2O$, $—CH(CH_3)S$, $—C(CH_3)_2S$, $—CH_2—NH—$, and $—CH_2N(CH_3)—$; $R^5$ and $R^{5a}$ are both hydrogen; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is benzoisothiazolyl, indazolyl, indolyl or benzothienyl, each optionally substituted with a group independently selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group independently selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group independently selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl, —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group independently selected from methyl, ethyl, propyl, isopropyl, cyclopropyl, methoxy, ethoxy, isopropoxy and cyclopropoxy; and $R^7$ is COOH.

The compounds of the invention can be prepared by a variety of procedures known in the art and those described below. The products of each step in the Scheme below can be recovered by conventional methods including extraction, evaporation, precipitation, chromatography, filtration, trituration, crystallization, and the like. In the scheme below all substituents, unless otherwise indicated, are as previously defined and suitable reagents are well known and appreciated in the art.

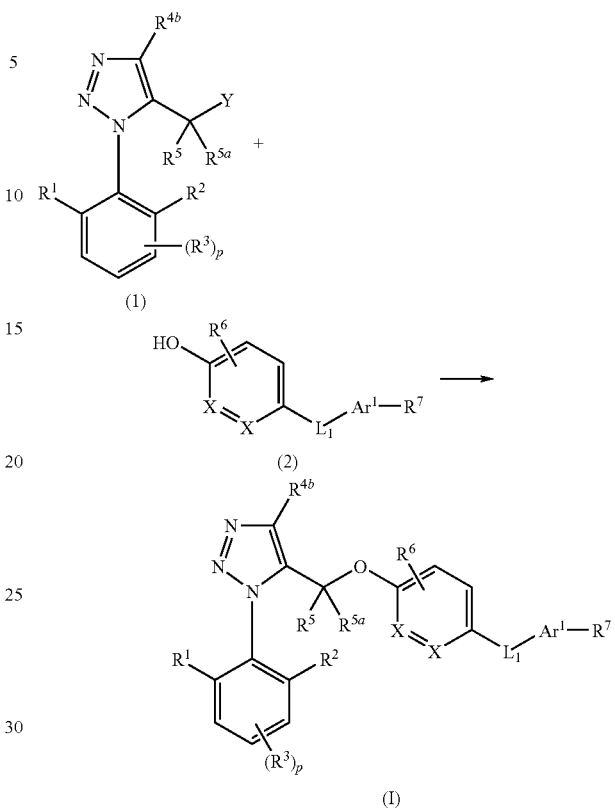

Scheme 1

Scheme 1 depicts the reaction of an appropriate compound of formula (1) with an appropriate compound of formula (2) to give a compound of formula (I). The reaction in Scheme 1 can be carried out by at least two variants discussed below.

In the first variant, an appropriate compound of formula (1) is one in which $R^1$, $R^2$, $R^3$, p, $R^{4b}$, $R^5$, and $R^{5a}$ are defined for formula I, and Y is —OH and an appropriate compound of formula (2) is one in which $R^6$, $R^7$, each X, $L_1$, and $Ar^1$ are as defined in formula (I) or a group which gives rise to $R^7$ as defined in formula (I), for example, by formation of an ester, amide, sulfonamide, or acid.

For example, a compound of formula (1) is reacted with a compound of formula (2) in a Mitsunobu reaction using a suitable diazo reagent, such as DEAD or ADDP, and the like, and a suitable phosphine reagent such as triphenyl phosphine or tributylphosphine, and the like. Such reactions are carried out in a suitable solvent, such as toluene, tetrahydrofuran, and the like. Generally, the reactions are carried out at temperatures of from about 0° C. to 50° C. Typical stoichiometry is for this reaction is, based on the compound of formula (1), about 1 to 2 equivalents of a compound of formula (2) and about 1 to 2 equivalents each of the diazo and phosphine reagents.

In the second variant, an appropriate compound of formula (1) is one in which $R^1$, $R^2$, $R^3$, p, $R^{4b}$, $R^5$, and $R^{5a}$ are defined for the invention and Y is a leaving group and an appropriate compound of formula (2) is as defined above. Suitable leaving groups are well-known in the art and include halides, particularly chloro, bromo, and iodo; and sulfonate esters, such as brosyl, tosyl, methanesulfonyl, and trifluoromethanesulfonyl.

For example, a compound of formula (1) is reacted with a compound of formula (2) in a suitable solvent, such as acetonitrile, dimethylformamide, tetrahydrofuran, pyridine, methylethyl ketone and the like. As will be readily appreciated an excess of a suitable base is usually used in the reaction, including sodium hydride, potassium carbonate, sodium carbonate, cesium carbonate, sodium bicarbonate, triethylamine, diisopropyethylamine. Such reactions generally are carried out at temperatures of about room temperature to about the reflux temperature of the chosen solvent and typically use from about 1 to 2 equivalents of the compound of formula (2).

In an optional step, a pharmaceutically acceptable salt of a compound of formula (I) is formed. The formation of such salts is well known and appreciated in the art.

As will be readily appreciated compounds of formula (1) and (2) can be readily prepared by methods that are well-known and established in the art including methods and procedures similar to those described herein. For example, compounds of formula (1) are prepared by the reaction of optionally substituted phenyl azide with an acetylene ester followed by reduction or a protected hydroxy acetylene and optionally conversion to a leaving group and compounds of formula (2) are prepared by carbon-carbon bond formation, reductive amination, coupling reaction, etc. Also, it is recognized that the steps required to prepare a compound of formula (2) can be carried out in any order, including after reaction of a partial compound of formula (2) with a compound of formula (1), such that the later carried out carbon-carbon bond formation, reductive amination, coupling reaction, etc, provide a compound of formula I. As will be readily understood the steps to prepare the compounds of formula I is dependent upon the particular compound being synthesized, the starting compound, and the relative liability of the substituted moieties. Also contemplated are various protection and deprotection steps as may be required or beneficial for carrying out the reactions above. The selection and use of suitable protecting groups is well known and appreciated in the art (see for example, *Protecting Groups in Organic Synthesis*, Theodora Greene (Wiley-Interscience)).

The present invention is further illustrated by the following examples and preparations. These examples and preparations are illustrative only and are not intended to limit the invention in any way. The terms used in the examples and preparations have their normal meanings unless otherwise designated. All chromatography is performed using silica gel, unless otherwise indicated.

Assay

The following assay protocols and results demonstrate the utility, in vitro and in vivo efficacy of the compounds and/or methods of the current invention and are provided for the purpose of illustration and not meant to be limiting in any way.

The following abbreviations used herein are defined as follows. "LDL" is: Low Density Lipoprotein; "HDL" is High Density Lipoprotein; "VLDL" is Very Low Density Lipoprotein; "LDLR-/-" is Low Density Lipoprotein receptor deficient; "DMEM" is Dulbecco's Modified Eagle's Medium; "GAPDH" is glyceraldehyde-3-phosphate dehydrogenase; "NaCMC" is sodium carboxymethylcellulose; "SLS" is sodium lauryl sulfate; "FPLC" is fast protein liquid chromatography; "PBS" is phosphate buffered saline; "VLDL-C" is Very Low Density Lipoprotein-Cholesterol; "HDL-C" is High Density Lipoprotein-Cholesterol.

bDNA Assay for SHP mRNA

FXR is a key, direct transcriptional regulator of the Small Heterodimer Partner (SHP) gene, accession number NM_021969, an atypical member of the nuclear receptor family that lacks a DNA-binding domain. SHP interacts with several conventional and orphan members of the nuclear receptor superfamily, including retinoid receptors and thyroid hormone receptor. SHP inhibits transactivation potential of superfamily members with which it interacts. FXR and SHP both have been found to control genes involved in hepatic cholesterol catabolism, triglyceride synthesis, and bile acid transport. Since FXR directly transactivates transcription of the SHP gene, the SHP branched DNA method (bDNA) quantitates FXR activation by ligands. Thus, increased expression of SHP mRNA, as determined by increase bDNA signal, signifies engagement of FXR by an agonist.

Plate human hepatocarcinoma Huh7 cells grown in DMEM:F12 with 10% fetal bovine serum and in 96 well plate at the density of $1\times10^5$/well. After overnight incubation, treat the cells with test compounds at various concentrations for 24 hours. Perform the bDNA assay according to the manufacturer protocol (Panomics, Fremont, Calif.) for the QuantiGene® High Volume Kit. After challenging the cells with a compound of the invention, lyse the cells with QuantiGene® lysis buffer containing the SHP mRNA oligonucleotides described below. Appropriate bDNA oligonucleotide reagents (capture extenders (CEs), label extenders (LEs), and blockers (BLs)) may be designed and synthesized for detecting human SHP mRNA by Panomics (Fremont, Calif.).

Incubate the lysis buffer for 15-minute at 37° C., then transfer 100 µL of the lysate from each well to the corresponding wells of the capture plate. Incubate the capture plate overnight at 53° C. Wash the capture plate twice with QuantiGene® wash buffer followed by addition of 100 µL/well QuantiGene® amplifier working reagent. Incubate the plate for 60 minutes at 46° C. followed by two washes. Label the mRNA to be measured by addition of 100 µL QuantiGene® label probe working buffer then incubate for 60 minutes at 46° C. Wash the capture plate twice and add 100 µL/well QuantiGene® substrate plus QuantiGene® enhancer reagent. Incubate the plates at 37° C. for up to 30 minutes and then read on a luminometer (Packard Fusion Alpha, 1 second detection) to detect the luminescent signal. Calculate $EC_{50}$ values i.e. effective response relative to maximal response. Exemplified compounds are effective as FXR modulators based on the above assay at an $EC_{50}$ of 2 uM or less. For example the compound of example 42 exhibits SHP gene activation $EC_{50}$ of about 370 nM.

LDLR-/- Serum Lipid Modulation

Acclimate animals for two weeks prior to study initiation. House mice individually in polycarbonate cages with filter tops, and maintain mice on a 12:12 hour light-dark cycle (lights on at 6:00 AM) at 21° C. Provide deionized water ad libitum and maintain for two weeks on 'western diet' TD 88137 Diet (42% fat, 0.15% cholesterol, Harlan Teklad) ad libitum. Optimize groups of five ten-week-old male LDLR-/- mice based on serum triglyceride and cholesterol levels. Dose groups once daily by oral gavage with various doses of the test compound dissolved in 5% EtOH/5% Solutol in NaCMC (1%), SLS (0.5%), antifoam (0.05%), Povidone (0.085%) for seven days. At the end of the seven-day dosing period, collect blood by cardiac puncture after asphyxiation in a $CO_2$ chamber. Measure serum triglycerides, glucose, and total cholesterol using standard clinical chemistry instrumentation and reagents [Hitachi 912 instrument with reagent kits (Roche, Indianapolis, Ind.)]. Assay pooled serum samples by FPLC analysis for lipoprotein cholesterol fraction values (VLDL, LDL, HDL) by separation on a size exclusion column with in-line determination of cholesterol. Lipoproteins were separated by fast protein liquid chromatography, and cholesterol was quantitated with an in-line detection system. Briefly, 35 µL plasma samples/50 µL pooled sample was applied to a Superose 6 HR 10/30 size exclusion column (Amersham Pharmacia Biotech, Piscataway, N.J.) and eluted with PBS, pH 7.4 (diluted 1:10), containing 5 mM EDTA, at 0.5 mL/min. Cholesterol reagent from Roche Diagnostics (Indianapolis, Ind.) at 0.16 mL/min was mixed with the column effluent through a T connection; the mixture was then passed through a 15 m×0.5 mm knitted tubing reactor (Aura Industries, New York, N.Y.) immersed in a 37 C water bath. The colored product produced in the presence of cholesterol was monitored in the flow stream at 505 nm, and the analog voltage from the monitor was converted to a digital signal for collection and analysis. The change in voltage corresponding to change in cholesterol concentration was plotted vs. time, and the area under the curve corresponding to the elution of VLDL-C and HDL-C was calculated using Turbochrome (version 4.12F12) software from PerkinElmer (Norwalk, Conn.).

In this assay, tested compounds of the invention reduce total cholesterol up to 84% and triglycerides up to 86% when dosed at 10 mg/kg. More specifically, the compound of Example 13 lowers total cholesterol by 60% and triglycerides by 63% when dosed at 10 mg/kg.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.1 mg to about 1000 mg/day of a compound of the present invention.

The compounds of this invention may be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of the invention, or a pharmaceutically acceptable salt thereof, and a pharmaceutically acceptable carrier, diluent, or excipient.

One skilled in the art can readily select the proper form and route of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions. The total active ingredients in such composition comprises from 0.1% to 99.9% by weight of the formulation.

Compounds of the invention may be formulated as elixirs or solutions for convenient oral administration or as solutions appropriate for parenteral administration, for example, by intramuscular, subcutaneous or intravenous routes. Additionally, the compounds may be formulated as sustained release dosage forms and the like. The formulations can be constituted such that they release the active ingredient only or preferably in a particular physiological location, possibly over a period of time. The coatings, envelopes, and protective matrices may be made, for example, from polymeric substances or waxes.

PREPARATIONS AND EXAMPLES

The following preparations and examples further illustrate the invention.

The following abbreviations used herein are defined according to Aldrichimica Acta, Vol 17, No. 1, 1984. Other abbreviations are defined as follows. "MeOH" is methanol; "EtOH" is ethanol; "EtOAc" is ethyl acetate; "Et$_2$O" is diethyl ether; "hex" is hexane; "DCE" is dichloroethane; "TMSCHN$_2$" is (trimethylsilyl)diazomethane; "ADDP" is 1,1-(Azodicarbonyl)dipiperidine; "dppf" is diphenylphosphinoferrocene; "dba" is dibenzylidineacetone; "THF" is tetrahydrofuran; "TBAF" is tetrabutylammonium fluoride; "OAc" is acetate; "DCE" is dichloroethane.

All compounds are named using ChemDraw Ultra 7.0 available from CambridgeSoft Corporation, Cambridge, Mass.

PREPARATIONS

Preparation 1

2-Azido-1,3-dichloro-benzene

Method 1

To a 0° C. solution of 2,6-dichloroaniline (2.00 g) in ethyl acetate (40 mL) is added concentrated hydrochloric acid (12 mL). The reaction is stirred for 10 min. To this solution is added a solution of sodium nitrite (2.55 g) in water (7.5 mL) over 3 min. Upon completion of the addition, the reaction is stirred for an additional 30 min. A solution of sodium azide (2.41 g) in water (8 mL) is added over 5 min. After 30 min, pH 7 buffer (50 mL) is added and the reaction is transferred to a separatory funnel. The layers are separated and the aqueous layer is extracted with ethyl acetate. The organic layers are combined and washed with brine, dried over sodium sulfate, filtered, and concentrated under reduced pressure to give the title compound (2.11 g). $^1$H NMR (400 MHz, CDCl$_3$) δ 7.3-7.27 (d, 2H), 7.07-7.02 (t, 1H)

Method 2

A solution of 2,6-dichloroaniline (100 g, 617 mmol) in MTBE (1 L) is added via addition funnel over 30 minutes to commercial hydrogen chloride (600 mL). The white suspension is stirred 15 minutes and is cooled to 0° C. A solution of sodium nitrite (42.5 g, 617 mmol) in water (150 mL) is added dropwise via addition funnel. After stirring at 0° C. for 30 minutes, a solution of sodium azide (40.1 g, 617 mmol) in water (150 mL) is added. After the addition is completed (45 minutes), the mixture is stirred at 5-10° C. for 30 minutes. The reaction mixture is basified (pH 12) with 50% aq. NaOH, and is stirred for 30 more minutes. The phases are separated and the aqueous layer is extracted three times with MTBE. The combined organic layers are dried over magnesium sulfate and filtered. Toluene (1 L) is added to the organic layer and the solution is concentrated under reduced pressure to a volume of 760 mL to yield the title compound (115 g, 100% conversion, 0.8M solution) as a toluene solution. ES/MS m/e 188 (M+1).

The following compounds are prepared essentially according to the preparation of 2-Azido-1,3-dichloro-benzene via method 1 using appropriate starting material. Preparation 1A: 2-Azido-1-chloro-3-fluoro-benzene; Preparation 1B:

1-Azido-2-trifluoromethoxy-benzene; Preparation 1C: 1-Azido-2-trifluoromethyl-benzene.

Preparation 2

2-Azidomethyl-1,3-dichloro-benzene

To a solution of 2,6-dichlorobenzylbromide (0.50 g) in dimethylformamide (5 mL) is added sodium azide (0.41 g). The reaction is heated to 55° C. overnight. The resulting solution is cooled to room temperature and is concentrated under reduced pressure. The residue is dissolved in ethyl acetate, washed with water and brine, dried over sodium sulfate, filtered, and concentrated under reduced pressure to give the title compound (0.37 g). $^1$H NMR (400 MHz, CDCl$_3$) δ 7.45-7.40 (d, 2H), 7.30-7.25 (t, 1H), 4.73 (s, 2H).

Preparation 3

4-Methyl-pent-2-ynoic acid ethyl ester

To a solution of the isopropyl alkyne (6.32 g), cooled in a dry-ice/acetone bath, in tetrahydrofuran (200 mL) is added 1.6 M N-butyl lithium solution (63.8 mL). After 1 h, ethyl chloroformate (9.33 mL) is added and the reaction mixture is stirred for an additional 1.5 h. The reaction mixture is allowed to warm to room temperature and is quenched with saturated ammonium chloride solution. The reaction is extracted two times with ethyl acetate. The organic layers are combined, washed with brine, dried over sodium sulfate, filtered, and concentrated under reduced pressure to give the title compound (11.5 g). $^1$H NMR (400 MHz, CDCl$_3$) δ 3.75 (s, 3H), 2.8-2.65 (m, 1H), 1.25-1.23 (d, 6H).

The following compound is prepared essentially according to the preparation of 4-Methyl-pent-2-ynoic acid ethyl ester using the appropriate starting material.

Preparation 3A: Cyclopropyl-propynoic acid methyl ester.

Preparation 4

3-(2,6-Dichloro-phenyl)-5-isopropyl-3H-[1,2,3]triazole-4-carboxylic acid ethyl ester A solution of 2-azido-1,3-dichloro-benzene (1.0 g) and 4-methyl-pent-2-ynoic acid ethyl ester (1.8 g) in toluene (5 mL) is heated to 120° C. overnight. Two regioisomers are observed in a range of 1:1 to 3:1 in favor of the desired product. The reaction is concentrated under reduced pressure and the residue is purified by flash chromatography, eluting with 5% ethyl acetate in hexanes. $^1$H NMR (400 MHz, CDCl$_3$) δ 7.48 (d, 2H), 7.42 (t, 1H), 4.22 (q, 2H), 3.64 (m, 1H), 1.46 (d, 6H), 1.15 (t, 3H).

The following compounds are prepared by methods similar to those described in the preparation of 3-(2,6-Dichloro-phenyl)-5-isopropyl-3H-[1,2,3]triazole-4-carboxylic acid ethyl ester using the appropriate starting material.

Preparation 4A: 5-Cyclopropyl-3-(2,6-dichloro-phenyl)-3H-[1,2,3]triazole-4-carboxylic acid methyl ester; Preparation 4B: 3-(2,6-Dichloro-phenyl)-5-methyl-3H-[1,2,3]triazole-4-carboxylic acid methyl ester: Preparation 4C: 3-(2,6-dichloro-phenyl)-5-isopropyl-3H-[1,2,3]triazole-4-carboxylic acid ethyl ester; Preparation 4D: 5-Isopropyl-3-(2-trifluoromethoxy-phenyl)-3H-[1,2,3]triazole-4-carboxylic acid ethyl ester; Preparation 4E: 5-Isopropyl-3-(2-trifluoromethyl-phenyl)-3H-[1,2,3]triazole-4-carboxylic acid ethyl ester Preparation 4F: 5-Cyclopropyl-3-(2,6-dichloro-phenyl)-3H-[1,2,3]triazole-4-carboxylic acid methyl ester; Preparation 4G: 5-Cyclopropyl-3-(2-trifluoromethoxy-phenyl)-3H-[1,2,3]triazole-4-carboxylic acid ethyl ester (64%), ES/MS m/e 342.0 (M+1).

Preparation 5

[3-(2,6-Dichloro-phenyl)-5-isopropyl-3H-[1,2,3]triazol-4-yl]-methanol

To a 0° C. solution of 3-(2,6-dichloro-phenyl)-5-isopropyl-3H-[1,2,3]triazole-4-carboxylic acid ethyl ester (2.88 g) in THF (25 mL) is added 1 M DIBAL in toluene (38 mL). The reaction is allowed to warm to room temperature. Upon completion, the reaction mixture is quenched slowly with water and is acidified with 1 N HCl. The resulting solution is extracted two times with ethyl acetate. The combined organic layers are washed with brine, dried over sodium sulfate, filtered, and concentrated under reduced pressure to give the title compound (2.26 g). ES/MS (m/e) 284 (M+0), 286 (M+2); mp: 154-155° C.

The following compounds are prepared essentially according to the preparation of [3-(2,6-Dichloro-phenyl)-5-isopropyl-3H-[1,2,3]triazol-4-yl]-methanol using the appropriate starting material.

Preparation 5A: [3-(2,6-Dichloro-phenyl)-5-methyl-3H-[1,2,3]triazol-4-yl]-methanol, $^1$H NMR (400 MHz, CDCl$_3$) δ 7.54 (m, 3H), 4.57 (s, 2H), 2.48 (s, 3H); Preparation 5B: [3-(2,6-dichloro-phenyl)-5-isopropyl-3H-[1,2,3]triazol-4-yl]-methanol, $^1$H NMR (400 MHz, CDCl3) δ 7.50 (m, 1H), 7.41 (dd, 1H), 7.24 (d, 1H), 4.60 (q, 2H), 3.20 (m, 1H), 1.45 (d, 6H); Preparation 5C: [5-Isopropyl-3-(2-trifluoromethoxy-phenyl)-3H-[1,2,3]triazol-4-yl]-methanol, $^1$H NMR (400 MHz, CDCl3) δ 7.62 (m, 2H), 7.50 (m, 2H), 4.60 (s, 2H), 3.19 (m, 1H), 1.41 (d, 6H); Preparation 5D: [5-Isopropyl-3-(2-trifluoromethyl-phenyl)-3H-[1,2,3]triazol-4-yl]-methanol, $^1$H NMR (CDCl3) δ 7.87 (d, 1H), 7.72 (m, 2H), 7.51 (d, 1H), 4.54 (d, 2H), 3.19 (m, 1H), 1.43 (d, 6H); Preparation 5E: [5-Cyclopropyl-3-(2,6-dichloro-phenyl)-3H-[1,2,3]triazol-4-yl]-methanol ES/MS (m/e): 284.0 (M+0), 286.0 (M+2); Preparation 5F: [5-Cyclopropyl-3-(2-trifluoromethoxy-phenyl)-3H-[1,2,3]triazol-4-yl]methanol (95%), ES/MS m/e 300.0 (M+1).

Preparation 6

5-Chloromethyl-1-(2,6-dichloro-phenyl)-4-isopropyl-1H-[1,2,3]triazole

To a solution of [3-(2,6-dichloro-phenyl)-5-isopropyl-3H-[1,2,3]triazol-4-yl]-methanol (0.100 g) in dichloromethane (2 mL) and carbon tetrachloride (2 mL) is added triphenyl phosphine (0.275 g). Upon completion, the reaction is concentrated under reduced pressure. The residue is dissolved in dichloromethane to aid in loading solubility and is purified via filter chromatography eluting with 10% ethyl acetate in toluene to give the desired product (0.091 g, 86%). $^1$H NMR (400 MHz, CDCl3) δ 7.58-7.54 (d, 2H), 7.52-7.50 (t, 1H), 4.48 (s, 2H), 3.24-3.21 (m, 1H), 1.51-1.49 (d, 6H).

Preparation 7

3-(2,6-Dichloro-phenyl)-3H-[1,2,3]triazole-4-carbaldehyde

Step A

A solution of 2-azido-1,3-dichloro-benzene (4.00 g, 1 equiv) and 3-trimethylsilanyl-prop-2-yn-1-ol (6.29 mL, 2 equiv) in toluene (10 mL) is heated to 120° C. for 23 h. The reaction mixture is allowed to cool to room temperature and is diluted with 100 mL methylene chloride. The solution is adsorbed onto diatomaceous earth and is purified via flash chromatography eluting with hexanes/ethyl acetate (85:15 to 20:80) to give [3-(2,6-Dichloro-phenyl)-3H-[1,2,3]triazol-4-yl]-methanol (2.30 g, 44%) as an off-white solid.

Step B

To a solution of [3-(2,6-dichloro-phenyl)-3H-[1,2,3]triazol-4-yl]-methanol (1.87 g, 1 equiv) in methylene chloride (110 mL) is added Dess-Martin oxidant (4.20 g, 1.3 equiv). The reaction mixture is allowed to stir at room temperature for 3 h. The reaction is incomplete as evidenced by TLC. The reaction mixture is treated with Dess-Martin oxidant (1.20 g). The reaction mixture is allowed to stir at room temperature for an additional 2 h. The reaction mixture is treated with 80 mL 1.5 N sodium hydroxide and 40 mL diethyl ether. The resulting solution is allowed to stir at room temperature for ten minutes. The reaction mixture is diluted with 120 mL water and extracted three times with chloroform. The combined organic layers are dried over magnesium sulfate and filtered though a plug of silica gel eluting with chloroform/ethyl acetate (3:1, 200 mL). The filtrate is concentrated under reduced pressure to give the title compound (1.76 g, 94%) as a white solid.

Preparation 8

Methanesulfonic acid 3-(2,6-dichloro-phenyl)-5-isopropyl-3H-[1,2,3]triazol-4-ylmethyl ester To a solution of [3-(2,6-dichloro-phenyl)-5-isopropyl-3H-[1,2,3]triazol-4-yl]-methanol (0.100 g) in dichloromethane (2 mL) is added $Et_3N$ (0.25 mL) followed by methanesulfonyl chloride (0.075 mL). The reaction mixture is stirred at room temperature for 2 h. The reaction is diluted with ethyl acetate (20 mL) and washed with water (2×20 mL). The organic layer is dried ($Na_2SO_4$) and concentrated under reduced pressure to give the title compound (101 mg). $^1H$ NMR (400 MHz, $CDCl_3$): δ 7.40-7.60 (m, 3H), 5.10 (s, 2H), 3.20-3.30 (m, 1H), 2.85 (s, 3H), and 1.40-1.50 (d, 6H).

Preparation 9

5-(4-Bromo-3-methyl-phenoxymethyl)-1-(2,6-dichloro-phenyl)-4-isopropyl-1H-[1,2,3]triazole To a solution of [3-(2,6-dichloro-phenyl)-5-isopropyl-3H-[1,2,3]triazol-4-yl]-methanol (300 mg, 1.05 mmol) in toluene (4 mL) are added 4-bromo-3-methyl-phenol (196 mg, 1.05 mmol) and tri-n-butylphosphine (394 μL, 1.58 mmol). The reaction mixture is cooled to 0° C. To the reaction mixture is added 1,1'-(Azocarbonyl)-dipiperidine (399 mg, 1.58 mmol) and the reaction mixture is warmed to room temperature. After 6 h, the reaction mixture is concentrated and the residue is chromatographed eluting with 10% to 20% EtOAc/hexanes to yield the title compound (324 mg, 68%). LC-ES/MS m/e 455.7 (M+1).

The following compounds are prepared essentially according to the preparation of 5-(4-Bromo-3-methyl-phenoxymethyl)-1-(2,6-dichloro-phenyl)-4-isopropyl-1H-[1,2,3]triazole using the appropriate starting material.

Preparation 9A: 1-(2,6-Dichloro-phenyl)-5-(4-iodo-phenoxymethyl)-4-isopropyl-1H-[1,2,3]triazole, LC-ES/MS m/e 488.0 (M+1), $^1H$ NMR (300 MHz, $CDCl_3$) δ 7.5 (m, 5H), 6.5 (d, 2H), 4.9 (s, 2H), 3.2 (p, 1H), 1.4 (d, 6H); Preparation 9B: 1-{4-[3-(2,6-Dichloro-phenyl)-5-isopropyl-3H-[1,2,3]triazol-4-ylmethoxy]-2-methyl-phenyl}-ethanone, LC-ES/MS m/e 418.0 (M+1); Preparation 9C, 1-{4-[3-(2-Chloro-6-fluoro-phenyl)-5-isopropyl-3H-[1,2,3]triazol-4-ylmethoxy]-2-methyl-phenyl}-ethanone LC-ES/MS m/e 402.0 (M+1); Preparation 9D, 2-{4-[3-(2,6-Dichloro-phenyl)-5-isopropyl-3H-[1,2,3]triazol-4-ylmethoxy]-phenyl}-propan-2-ol; Preparation 9E, 6-{4-[5-Cyclopropyl-3-(2,6-dichloro-phenyl)-3H-[1,2,3]triazol-4-ylmethoxy]-2-methyl-phenyl}-1-isopropyl-1H-indole-3-carboxylic acid methyl ester, ES/MS m/e 590.8 (M+1).

Preparation 10

1-{4-[3-(2,6-Dichloro-phenyl)-5-isopropyl-3H-[1,2,3]triazol-4-ylmethoxy]-2-methyl-phenyl}-ethanol To a 0° C. solution of 1-{4-[3-(2,6-dichloro-phenyl)-5-isopropyl-3H-[1,2,3]triazol-4-ylmethoxy]-2-methyl-phenyl}-ethanone (314 mg, 0.751 mmol) in THF/MeOH (6 mL/1 mL) is added sodium borohydride (116 mg, 3.04 mmol). The reaction is warmed to room temperature overnight. The reaction is concentrated and the residue is partitioned between EtOAc (100 mL) and 1 N HCl (20 mL). The aqueous layer is extracted with EtOAc (100 mL) and the combined organic layers are washed with brine, dried ($MgSO_4$), filtered, and concentrated under reduced pressure. The residue is purified via chromatography (40 g $SiO_2$, 20% to 40% EtOAC/Hexanes) to yield the title compound (298 mg, 94%). LC-ES/MS m/e 419.7 (M+1).

The following compound is prepared essentially according to the preparation of 1-{4-[3-(2,6-Dichloro-phenyl)-5-isopropyl-3H-[1,2,3]triazol-4-ylmethoxy]-2-methyl-phenyl}-ethanol using the appropriate starting material.

Preparation 10A: 1-{4-[3-(2-Chloro-6-fluoro-phenyl)-5-isopropyl-3H-[1,2,3]triazol-4-ylmethoxy]-2-methyl-phenyl}-ethanol.

Preparation 11

2-{4-[3-(2,6-Dichloro-phenyl)-5-isopropyl-3H-[1,2,3]triazol-4-ylmethoxy]-2-methyl-phenyl}-propan-2-ol To a −78° C. solution of 1-{4-[3-(2,6-dichloro-phenyl)-5-isopropyl-3H-[1,2,3]triazol-4-ylmethoxy]-2-methyl-phenyl}-ethanone (500 mg, 1.19 mmol) in THF (12 mL) is added methylmagnesium bromide (2.0 mL, 5.98 mmol, 3.0 M in THF) dropwise. The reaction mixture is warmed to room temperature. After 4 h, the reaction is cooled to 0° C., quenched with $NH_4Cl$ and warmed to room temperature. The reaction mixture is concentrated and the residue is partitioned between $Et_2O$ and 1N HCl. The aqueous layer is extracted with $Et_2O$ and the combined organic layers are washed with brine, dried ($MgSO_4$), filtered, concentrated and chromatographed eluting with 0% to 30% EtOAC/Hexane to yield the title compound (414 mg, 80%). $^1H$ NMR (400 MHz, $CDCl_3$) δ 7.49-7.46 (m, 2H), 7.43-7.38 (m, 1H), 7.23-7.19 (m, 2H), 6.70 (d, 1H, J=8.8 Hz), 4.89 (s, 2H), 3.20 (sept, 1H, J=6.6 Hz), 2.04 (s, 3H), 1.53 (s, 6H), 1.45 (d, 6H, J=6.6 Hz).

The following compounds are prepared essentially according to the preparation of 2-{4-[3-(2,6-Dichloro-phenyl)-5-isopropyl-3H-[1,2,3]triazol-4-ylmethoxy]-2-methyl-phenyl}-propan-2-ol using the appropriate starting material.

Preparation 11A: 2-{4-[3-(2,6-Dichloro-phenyl)-5-isopropyl-3H-[1,2,3]triazol-4-ylmethoxy]-phenyl}-propan-2- ol, $^1$H NMR (400 MHz, CDCl$_3$) δ 7.48 (d, 1H, J=1.3 Hz), 7.46 (s, 1H), 7.39 (dd, 1H, J=9.2, 7.0 Hz), 7.35 (d, 2H, J=8.8 Hz), 6.73 (d, 2H, J=8.8 Hz), 4.90 (s, 2H), 3.19 (sept, 1H, J=7.0 Hz), 1.54 (s, 6H), 1.44 (d, 6H, J=7.0 Hz); Preparation 11B: 2-{4-[3-(2,6-Dichloro-phenyl)-5-isopropyl-3H-[1,2,3]triazol-4-ylmethoxy]-3-methyl-phenyl}-propan-2-ol, $^1$H NMR (400 MHz, CDCl$_3$) δ 7.48 (d, 1H, J=1.8 Hz), 7.46 (s, 1H), 7.40 (dd, 1H, J=9.2, 6.6 Hz), 7.23-7.19 (m, 2H), 6.70 (d, 1H, J=8.8 Hz), 4.89 (s, 2H), 3.21 (sept, 1H, J=7.0 Hz), 2.04 (s, 3H), 1.54 (s, 6H), 1.45 (d, 6H, J=7.0 Hz).

Preparation 12

3-Methyl-4-(4,4,5,5-tetramethyl-[1,3,2]dioxaborolan-2-yl)-phenol

A mixture of tricyclohexylphosphine (525 mg, 1.87 mmol), palladium bis(dibenzylidine)acetone (460 mg, 0.801 mmol) and dioxane (200 ml) is stirred at room temperature for one half hour. Added are 4-bromo-3-methyl-phenol (5.00 g, 26.7 mmol), pinacolborane (7.45 g, 40.1 mmol) and potassium acetate (3.93 g, 40.1 mmol). The reaction mixture is heated to 80° C. for 20 hours and is cooled to room temperature. The reaction mixture is diluted with water and extracted with ether. The combined ether fractions are washed with brine, dried (MgSO$_4$) and evaporated. The residue is purified using flash chromatography on silica gel eluting with 0 to 2% MeOH/CH$_2$Cl$_2$, to yield g the title compound (1.6 g, 47%). An additional 2.76 g of the title compound is provided by a second purification of impure fractions by flash chromatography to yield a total of 4.36 g (70%) of the title compound. ES/MS m/e 233.3 (M−1).

Preparation 13

6-Bromo-1H-indole-3-carboxylic acid methyl ester

To a solution of 6-bromoindole-3-carboxylic acid (960 mg, 4.00 mmol) in methanol (9.5 mL) is added (trimethylsilyl)diazomethane (2.0 M solution in hexanes, ca 9 mL) over two minutes at room temperature. The yellow mixture is concentrated under reduced pressure. The residue is redissolved in methanol and concentrated under reduced pressure. This process is repeated several times to give the title compound as a solid (100%). ES/MS m/e 256.0 (M+2).

The following compound is prepared essentially according to the preparation of 6-bromo-1H-indole-3-carboxylic acid methyl ester using the appropriate starting material. Preparation 13A: 6-Bromo-benzo[b]thiophene-2-carboxylic acid methyl ester, $^1$H NMR (400 MHz, CDCl$_3$) δ 7.99 (m, 2H), 7.70 (d, 1H), 7.50 (d, 1H), 3.92 (s, 3H).

Preparation 14

6-Bromo-1-methyl-1H-indole-3-carboxylic acid methyl ester

To a mixture of 5-bromo-1H-indole-3-carboxylic acid methyl ester (100 mg, 0.394 mmol), potassium carbonate (163 mg, 1.18 mmol) in DMF is added iodomethane (30 μL, 0.47 mmol). The reaction mixture is stirred for 1.5 hours. Additional iodomethane (10 μL) is added and the reaction is stirred for 30 minutes. The reaction mixture is diluted with dichloromethane and filtered. The filtrate is concentrated under high vacuum, diluted with ethyl acetate, and concentrated to give 105 mg (99%) of the title compound. ES/MS m/e 270.0 (M+2).

The following compound is prepared essentially according to the preparation of 6-bromo-1-methyl-1H-indole-3-carboxylic acid methyl ester, using the appropriate starting material.

Preparation 14A: 6-Bromo-1-isopropyl-1H-indole-3-carboxylic acid methyl ester, $^1$H NMR (400 MHz, CDCl$_3$) δ 8.02 (d, 1H), 7.88 (s, 1H), 7.53 (s, 1H), 7.33 (dd, 1H), 4.64-4.33 (m, 1H), 3.88 (s, 3H), 1.52 (d, 6H).

Preparation 15

6-(4-Hydroxy-2-methyl-phenyl)-1-methyl-1H-indole-3-carboxylic acid methyl ester

A mixture of 3-methyl-4-(4,4,5,5-tetramethyl-[1,3,2]dioxaborolan-2-yl)-phenol (105 mg, 0.448 mmol), (6-bromo-1H-indol-3-yl)-acetic acid methyl ester (100 mg, 0.373 mmol), tetrakis(triphenylphosphine)palladium(0) (25 mg, 0.021 mmol), DMF (1.2 mL), ethanol (0.6 mL) and 2M aqueous potassium carbonate (0.6 mL) is heated to 80° C. for 6 hours. The reaction is cooled to room temperature, diluted with water, and acidified with 1 N HCl. The resulting solution is extracted with CH$_2$Cl$_2$. The combined organic layers are dried over anhydrous magnesium sulfate and concentrated. The residue is purified via radial chromatography eluting with CH$_2$Cl$_2$. A second purification of impure fractions is performed via radial chromatography eluting with 2% MeOH—CH$_2$Cl$_2$ to provide (78 mg, 74%) of the title compound. LC-ES/MS m/e 296.0 (M+1).

The following compounds are prepared essentially according to the preparation of 6-(4-Hydroxy-2-methyl-phenyl)-1-methyl-1H-indole-3-carboxylic acid methyl ester using the appropriate starting material.

Preparation 15A: 6-(4-Hydroxy-2-methyl-phenyl)-benzo[b]thiophene-3-carboxylic acid methyl ester; Preparation 15B: 6-(4-hydroxy-2-methyl-phenyl)-benzo[b]thiophene-2-carboxylic acid methyl ester, utilizing a 7:3 mixture of 6-bromo-benzo[b]thiophene-3-carboxylic acid methyl ester and 6-bromo-benzo[b]thiophene-2-carboxylic acid methyl ester, ES/MS m/e 297.0 (M−1); Preparation 15C: 6-(4-Hydroxy-2-methyl-phenyl)-benzo[b]thiophene-2-carboxylic acid methyl ester, ES/MS m/e 297.3 (M−1); Preparation 15E: 6-(4-Hydroxy-2-methyl-phenyl)-1-isopropyl-1H-indole-3-carboxylic acid methyl ester, ES/MS m/e 322.2 (M−1); Preparation 15D: 6-(4-Hydroxy-2-methyl-phenyl)-benzo[b]thiophene-2-carboxylic acid methyl ester, ES/MS m/e 297.3 (M−1).

Preparation 16

2- and 3-acetyl-6-bromobenzothiophene

To a solution of 6-bromobenzothiophene (20 g, 93.8 mmol) and acetyl chloride (8.84 g, 112.6 mmol) in 1,2-dichloroethane (120 mL) is added dropwise at room temperature, tin tetrachloride (1M in dichloromethane, 112.6 mmol, 112.6 mL) under nitrogen. After the addition is completed, the reaction mixture is stirred at room temperature overnight. The mixture is poured onto an ice/water bath and extracted with dichloromethane. The organic phase is washed with saturated NaHCO$_3$, water, and brine, dried over MgSO$_4$, and evaporated under reduced pressure. The crude residue is purified by flash chromatography on silica gel eluting with hexane/EtOAc 6:1 as eluent mixture. The title compound (12 g, 50%) is obtained as a 7:3 mixture of the two isomers:

3-acetyl-6-bromobenzothiophene and 2-acetyl-6-bromobenzothiophene. ES/MS m/e 256 (M+2).

Preparation 17

6-Bromobenzothiophene-3-carboxylic acid and 6-Bromobenzothiophene-2-carboxylic Acid To a 0° C. solution of sodium hydroxide (13.64 g, 341 mmol) in water (94 mL) is added slowly bromine (21.92 g, 137.18 mmol). The reaction mixture is stirred at 0° C. for 15 minutes. To the reaction mixture is added dropwise a solution of the mixture of 3-acetyl-6-bromobenzothiophene and 2-acetyl-6-bromobenzothiophene (10.00 g, 39.19 mmol) in dioxane (75 mL). The reaction mixture is stirred at room temperature for 2 hours. A solution of NaHSO$_3$ (40%, 50 mL) is added followed by HCl (10 mL) to give an orange solid. The solid is filtered off, and washed with water followed by hexanes to give 7 g (70%) of the mixture of both acids: 6-Bromobenzothiophene-3-carboxylic acid and 6-Bromobenzothiophene-2-carboxylic acid in a ratio 7:3. ES/MS m/e 258 (M+2).

Preparation 18

6-Bromobenzothiophene-3-carboxylic acid methyl ester and 6-Bromobenzothiophene-2-carboxylic acid methyl ester A solution of the mixture of 6-Bromobenzothiophene-3-carboxylic acid and 6-Bromobenzothiophene-2-carboxylic acid (6.5 g, 25.28 mmol) and sulfuric acid (4.65 g, 47.43 mmol) in MeOH (100 mL) is heated to 65° C. overnight. A light brown solid is visualized. The solution is cooled to room temperature and the solid formed is filtered off and washed with MeOH to give 5.6 g (83%) of the mixture of: 6-Bromobenzothiophene-3-carboxylic acid methyl ester and 6-Bromobenzothiophene-2-carboxylic acid methyl ester in a ratio 7:3. ES/MS m/e 272 (M+2).

Preparation 19

2'-Bromo-4'-hydroxy-biphenyl-4-carboxylic acid methyl ester

Step A

To 4'-methoxy-2'-nitro-biphenyl-4-carboxylic acid methyl ester (4.00 g) suspended in ethanol (150 mL) and ethyl acetate (150 mL) is added 5% palladium on carbon (0.300 g). The reaction mixture is placed under an atmosphere of hydrogen (50 psi) and shaken on a Parr apparatus. After 18 h, the reaction mixture is degassed with nitrogen and filtered though a plug of silica gel, eluting with 700 mL ethyl acetate and 600 mL methylene chloride. The filtrate is evaporated to give 2'-amino-4'-methoxy-biphenyl-4-carboxylic acid methyl ester (3.52 g, >99%) as a white solid.

Step B

To a solution of sodium nitrite (1.40 g) in dimethyl sulfoxide (50 mL) is added 2'-amino-4'-methoxy-biphenyl-4-carboxylic acid methyl ester (2.61 g). After 5 minutes, the reaction mixture is treated with a solution of 4.7 mL hydrobromic acid (48%) in 50 mL dimethyl sulfoxide. The reaction is allowed to stir at room temperature for 2 h. The reaction mixture is diluted with a solution of 20.0 g potassium carbonate dissolved in 400 mL water. The product is extracted five times with methylene chloride. The combined organic layers are dried over magnesium sulfate, filtered, and concentrated under reduced pressure. The residue is chromatographed eluting with hexanes/ethyl acetate (99:1 to 86:14) to give 2'-bromo-4'-methoxy-biphenyl-4-carboxylic acid methyl ester (1.00 g, 31%) as a white solid.

Step C

To a 0° C. solution of 2'-bromo-4'-methoxy-biphenyl-4-carboxylic acid methyl ester (0.200 g) in methylene chloride (5 mL) is added boron tribromide (0.176 mL). The reaction mixture is maintained at 0° C. for 2 h. The reaction mixture is slowly quenched with 50 mL methanol, diluted with 150 mL 2N hydrochloric acid, and extracted three times with methylene chloride. The combined organic layers are dried over magnesium sulfate, filtered, and concentrated under reduced pressure to give the title compound (0.180 g, 94%).

Preparation 20

4'-Hydroxy-2'-methyl-biphenyl-4-carboxylic acid methyl ester

To a solution of 4-bromo-3-methyl phenol (0.300 g, 1 equiv) in DMF (5 mL) are added 4-methylester phenyl boronic acid (0.58 g, 2 equiv), dppf (0.27 g, 0.3 equiv), palladium acetate (0.036 g, 0.1 equiv), and cesium carbonate (1.04 g, 2 equiv). The reaction mixture is heated to 75° C. for 1 h. The reaction is cooled to room temperature and is diluted with water. The resulting solution is extracted with ethyl acetate. The combined organic layers are combined and washed with brine, dried over sodium sulfate, filtered, and concentrated under reduced pressure. The crude residue is purified via flash chromatography eluting with 3% ethyl acetate in toluene to give the desired product (0.224 g, 58%). ES/MS m/e 241.3 (M−1).

The following list is prepared essentially according to the preparation of 4'-Hydroxy-2'-methyl-biphenyl-4-carboxylic acid methyl ester using the appropriate starting material.

Preparation 20A: 4'-Hydroxy-3'-methyl-biphenyl-4-carboxylic acid methyl ester;
Preparation 20B: 2'-chloro-4'-hydroxy-biphenyl-4-carboxylic acid methyl ester;
Preparation 20C: 2'-Fluoro-4'-hydroxy-biphenyl-4-carboxylic acid methyl ester;
Preparation 20D: 4'-hydroxy-2'-trifluoromethyl-biphenyl-4-carboxylic acid methyl ester;
Preparation 20E: 4'-Hydroxy-2'-nitro-biphenyl-4-carboxylic acid methyl ester'

Preparation 21

Trifluoro-methanesulfonic acid 2-(4-methoxy-phenyl)-benzo[b]thiophen-6-yl ester

To a solution of 2-(4-methoxy-phenyl)-benzo[b]thiophen-6-ol (512 mg, 2 mmol) in dichloromethane (20 mL) at 0° C. is added triethylamine (0.58 mL, 5 mmol) and trifluoromethanesulfonic anhydride (0.67 mL, 4 mmol). The reaction is stirred at ambient temperature overnight. The reaction mixture is concentrated and the residue is redissolved in EtOAc, is washed with 1N NaOH followed by 1N HCl. The organic layer is concentrated to give the title compound (800 mg).

Preparation 22

2-(4-Methoxy-phenyl)-benzo[b]thiophene-6-carboxylic acid methyl ester

A mixture of trifluoro-methanesulfonic acid 2-(4-methoxy-phenyl)-benzo[b]thiophen-6-yl ester (750 mg), palladium acetate (43 mg), 1,4-bis(diphenylphosphino)butane (97 mg), triethylamine (1.4 mL) in MeOH (8 mL) and DMSO (12 mL) is stirred under an atmosphere of carbon monoxide (100 psi) at 80° C. for 4 h. The reaction mixture is filtered though a diatomaceous earth pad and the filtrate is concentrated. The residue is purified by column chromatography on silica gel eluting with 0 to 20% EtOAc in hexanes to give the title compound (500 mg, 87%). LC-ES/MS m/e 321 (M+Na).

Preparation 23

2-(4-Hydroxy-phenyl)-benzo[b]thiophene-6-carboxylic acid methyl ester

To a solution of 2-(4-methoxy-phenyl)-benzo[b]thiophene-6-carboxylic acid methyl ester (500 mg, 1.7 mmol) in dichloromethane (15 mL) at 0° C. is added $BBr_3$ (4.2 mL, 1 M in dichloromethane). The reaction mixture is stirred at ambient temperature overnight. The reaction is quenched by the addition of methanol and concentrated under reduced pressure. The residue is partitioned between EtOAc and 1 N HCl. The organic layer is concentrated and the residue is purified via chromatography eluting with 0 to 25% EtOAc in hexanes to give the title compound (57 mg, 12%) as a tan solid. LC-ES/MS m/e 283 (M−1).

Preparation 24

5-(4-Hydroxy-2-methyl-phenyl)-4-methyl-thiophene-2-carboxylic acid methyl ester

Step A

To a mixture of 4-methoxy-2-methylphenylboronic acid (912 mg, 6 mmol), 5-bromo-4-methyl-thiophene-2-carboxylic acid methyl ester (1.1 g, 5 mmol) and $K_2CO_3$ (1.38 g, 10 mmol) in toluene (30 mL) and water (5 mL) is bubbled $N_2$ for 15 minutes followed by addition of tetrakis(triphenylphosphine) palladium (289 mg, 0.25 mmol). The reaction mixture is stirred at 80° C. under $N_2$ overnight. The reaction mixture is filtered through a diatomaceous earth pad eluting with EtOAc. The combined filtrate is concentrated and the residue is purified by column chromatography on silica gel eluting with 0-15% EtOAc in hexanes to give 5-(4-methoxy-2-methyl-phenyl)-4-methyl-thiophene-2-carboxylic acid methyl ester (540 mg, 39%). $^1$H NMR (CDCl$_3$): δ 7.63 (s, 1H), 7.15 (d, 1H, J=8.4 Hz), 6.82 (d, 1H, J=2.8 Hz), 6.78 (dd, 1H, J=2.8, J=8.4 Hz), 4.79 (bs, 1H), 3.88 (s, 3H), 3.83 (s, 3H), 2.17 (s, 3H), 2.02 (s, 3H).

Step B

To a 0° C. solution of 5-(4-methoxy-2-methyl-phenyl)-4-methyl-thiophene-2-carboxylic acid methyl ester (540 mg, 2 mmol) in dichloromethane (30 mL) is added BBr$_3$ in dichloromethane (1N, 5.0 mL) and the mixture is stirred at ambient temperature overnight. The reaction is quenched by addition of methanol and evaporated. The residue is purified by column chromatography on silica gel eluting with 0-20% EtOAc in hexanes to give the title compound (420 mg, 82%). $^1$H NMR (CDCl$_3$): δ 7.62 (s, 1H), 7.10 (d, 1H, J=7.9 Hz), 6.76 (s, 1H), 6.70 (d, 1H, J=7.9 Hz), 4.79 (bs, 1H), 3.88 (s, 3H), 2.15 (s, 3H), 2.02 (s, 3H).

The following compounds are prepared essentially according to the preparation 5-(4-hydroxy-2-methyl-phenyl)-4-methyl-thiophene-2-carboxylic acid methyl ester using the appropriate starting material.

Preparation 24A: 5-(4-Hydroxy-phenyl)-thiophene-2-carboxylic acid methyl ester, $^1$H NMR (DMSO-d$_6$): δ 9.87 (s, 1H), 7.74 (d, 1H, J=4.0 Hz), 7.57 (d, 2H, J=8.8 Hz), 7.40 (d, 1H, J=4.0 Hz), 6.83 (d, 2H, J=8.8 Hz), 3.81 (s, 3H).

Preparation 24B: 5-(4-Hydroxy-2-methyl-phenyl)-thiophene-2-carboxylic acid methyl ester, $^1$H NMR (DMSO-d$_6$): δ 9.71 (s, 1H), 7.76 (d, 1H, J=3.5 Hz), 7.26 (d, 1H, J=8.4 Hz), 7.17 (d, 1H, J=4.0 Hz), 6.72 (d, 1H, J=2.6 Hz), 6.67 (dd, 1H, J=2.6, J=8.4 Hz), 3.81 (s, 3H), 2.32 (s, 3H).

Preparation 25

4-{[(4-Hydroxy-2-methyl-phenyl)-methyl-amino]-methyl}-benzoic acid methyl ester To an ambient temperature solution of 4-amino-3-methyl-phenol (1.0 g, 8.12 mmol) in MeOH (77 mL) is added 4-formyl-benzoic acid methyl ester (1.47 g, 8.93 mmol) and decaborane (329 mg, 2.68 mmol). The reaction is stirred at room temperature. After 2 h, formaldehyde (1.23 mL, 16.93 mmol, 37% in water) and decaborane (329 mg, 2.68 mmol) are added to the reaction. The reaction mixture is stirred overnight. The reaction mixture is concentrated under reduced pressure and the residue is purified via chromatography to yield the title compound (2.07 g, 90%). LC-ES/MS m/e 286.2 (M+1).

The following compound is prepared essentially according to the preparation 54-{[(4-hydroxy-2-methyl-phenyl)-methyl-amino]-methyl}-benzoic acid methyl ester using the appropriate starting material Preparation 25A: 3-{[(4-Hydroxy-2-methyl-phenyl)-methyl-amino]-methyl}-benzoic acid methyl ester (74%), LC-ES/MS m/e 286.2 (M+1); Preparation 25 B: 4-{[(4-Hydroxy-2-methyl-phenyl)-methyl-amino]methyl}-2-trifluoromethyl-benzoic acid methyl ester (35% yield), LC-ES/MS m/e 340.0 (M+1).

Preparation 26

3-[2-(2-Chloro-4-hydroxy-phenyl)-vinyl]-benzoic acid methyl ester

To a solution of 3-vinylbenzoic acid methyl (0.300 g) ester in dimethylformamide (3 mL) are added 4-bromo-3-methyl phenol (0.35 g), tri(orthotoluyl)phosphine (0.06 g), Pd(dba)$_2$ (0.032 g), and triethylamine (0.26 mL). The reaction is heated to 100° C. overnight. Upon cooling to room temperature, the solvent is evaporated under reduced pressure. The residue is dissolved in ethyl acetate, washed with water and brine, dried over sodium sulfate, filtered, and concentrated under reduced pressure. The resulting residue is purified via filter chromatography on silica gel eluting with 300 mL toluene followed by 250 mL 10% ethyl acetate in toluene to give the title compound (0.210 g). $^1$H NMR (400 MHz, CDCl$_3$) δ 8.20 (s, 1H), 7.95-7.93 (d, 1H), 7.71-7.69 (d, 1H), 7.53-7.51 (d, 1H), 7.48-7.44 (t, 1H), 7.38-7.34 (d, 1H), 6.96-6.92 (d, 1H), 6.77-6.72 (m, 2H), 5.26 (broad s, 1H), 3.99 (s, 3H), 2.43 (s, 3H).

Preparation 27

2-Trimethylsilanylethynyl-benzoic acid methyl ester

To a solution of 2-iodo-benzoic acid methyl ester (792 mg, 3.02 mmol) in DMF (10 mL) are added trimethylsilylacetylene (854 µL, 6.04 mmol) and triethylamine (2.95 mL, 21.1 mmol). The reaction mixture is degassed for 20 minutes with a stream of nitrogen. Dichloro(bistriphenylphosphene) palladium (II) (212 mg, 0.302 mmol, 10 mol %) and copper (I) iodide (58 mg, 0.302 mmol, 10 mol %) are added and the reaction is heated to 80° C. After 3 h, the reaction is concentrated and the residue is chromatographed eluting with 0 to 5% EtOAc/Hexanes to yield the title compound (597 mg, 85%). GC/MS: 232.

The following list of compounds is prepared essentially according to the preparation of 2-trimethylsilanylethynyl-benzoic acid methyl ester using the appropriate starting material.

Preparation 27A: 3-Trimethylsilanylethynyl-benzoic acid methyl ester, GC/MS: 232; 4;

Preparation 27B: Trimethylsilanylethynyl-benzoic acid methyl ester, GC/MS: 232.

Preparation 28

2-Ethynyl-benzoic acid methyl ester

To a solution of 2-trimethylsilanylethynyl-benzoic acid methyl ester (540 mg, 2.32 mmol) in acetonitrile/water (20 mL/5 mL) is added cesium fluoride (1.41 g, 9.30 mmol). The reaction is stirred at room temperature. After 4 h, the reaction is concentrated and the residue is partitioned between EtOAc (100 mL) and 0.2N HCl (30 mL). The aqueous layer is extracted with EtOAc (100 mL) and the combined organic layers are washed with brine, dried (MgSO$_4$), filtered, and concentrated. The residue is chromatographed eluting with 0 to 5% EtOAc/Hexanes to yield the title compound (358 mg, 96%). GC/MS: 160.

The following compound is prepared essentially according to the preparation of 2-ethynyl-benzoic acid methyl ester using the appropriate starting material.

Preparation 28A: 3-Ethynyl-benzoic acid methyl ester, GC/MS: 160; Preparation 28B: 4-Ethynyl-benzoic acid methyl ester, GC/MS: 160.

Preparation 29

(4-Mercapto-phenyl)-acetic acid methyl ester

To an ambient temperature solution of 4-mercaptophenylacetic acid (5.0 g, 29.72 mmol) in MeOH (250 mL) is added sulfuric acid (1.25 mL). The reaction is stirred at room temperature overnight. The reaction mixture is concentrated and the residue is partitioned between Et$_2$O and water. The aqueous layer is extracted with Et$_2$O and the combined organic layers are washed with brine, dried (MgSO$_4$), filtered, concentrated and chromatographed eluting with 0% to 30% EtOAC/Hexane to yield the title compound (3.69 g, 68%). $^1$H NMR (400 MHz, CDCl$_3$) δ 7.21 (d, 2H, J=7.9 Hz), 7.12 (d, 2H, J=8.4 Hz), 3.66 (s, 3H), 3.54 (s, 2H).

Preparation 30

3-(4-Hydroxy-2-methyl-benzylamino)-benzoic acid ethyl ester

Step A

A mixture of 2-methyl-4-benzyloxy benzaldehyde (1.22 g, 5.39 mmol) and ethyl-3-amino benzoate (912 mg, 5.52 mmol) in glacial acetic acid (40 mL) is stirred for 30 minutes. To the mixture, sodium triacetoxy borohydride (1.25 g, 5.90 mmol) is added. After 20 hours, the mixture is concentrated and partitioned between ethyl acetate and saturated sodium bicarbonate. The layers are separated and the aqueous layer is extracted with ethyl acetate (2×). The combined ethyl acetate layers are dried (MgSO$_4$) and concentrated. The residue is purified by flash chromatography on 120 g silica with ethyl acetate in heptane gradient to provide benzyl intermediate (1.6 g, 80%).

Step B

To a solution of the benzyl intermediate from Step A (471 mg, 1.25 mmol) in ethyl acetate (20 mL) under nitrogen is added 10% palladium on carbon (80 mg). The reaction vessel is evacuated and filled with hydrogen (balloon) and stirred under hydrogen over night. The mixture is filtered over diatomaceous earth and concentrated under reduced pressure to provide the title product (300 mg, 84%). MS: 284.3 (M−1).

The following compound is prepared essentially according to the preparation of 3-(4-hydroxy-2-methyl-benzylamino)-benzoic acid ethyl ester using the appropriate starting material.

Preparation 30A: 4-(4-Hydroxy-2-methyl-benzylamino)-benzoic acid methyl ester, (546 mg, 91%), ES/MS m/e 270.3 (M−1).

Preparation 31

1-{4-[3-(2,6-Dichloro-phenyl)-5-isopropyl-3H-[1,2,3]triazol-4-ylmethoxy]-2-methyl-phenyl}-ethanone To a 0° C. suspension of 4'-hydroxy-2'-methylacetophenone (969 mg, 6.45 mmol), [3-(2,6-Dichloro-phenyl)-5-isopropyl-3H-[1,2,3]triazol-4-yl]-methanol (1.85 g, 6.45 mmol), tri-n-butylphosphine (2.42 ml, 9.73 mmol) in toluene (20 mL) is added ADDP (2.46 g, 9.73 mmol). The reaction mixture is warmed to room temperature and stirred overnight. The reaction mixture is concentrated and the residue is chromatographed eluting with 0% to 30% EtOAc/Hex to yield the title compound (1.71 mg, 63%). $^1$H NMR (400 MHz, CDCl$_3$) δ 7.75 (dd, 1H, J=8.5, 2.1 Hz), 7.72 (d, 1H, J=1.3 Hz), 7.49 (d, 1H, J=2.2 Hz), 7.47 (s, 1H), 7.41 (dd, 1H, J=9.2, 6.6 Hz), 6.78 (d, 1H, J=8.4 Hz), 4.99 (s, 2H), 3.22 (sept, 1H, J=7.0 Hz), 2.52 (s, 3H), 2.06 (s, 3H), 1.46 (d, 6H, J=7.0 Hz).

The following list of compounds is prepared essentially according to the preparation of 1-{4-[3-(2,6-Dichloro-phenyl)-5-isopropyl-3H-[1,2,3]triazol-4-ylmethoxy]-2-methyl-phenyl}-ethanone using the appropriate starting material.

Preparation 31A: 1-{4-[3-(2,6-Dichloro-phenyl)-5-isopropyl-3H-[1,2,3]triazol-4-ylmethoxy]-phenyl}-ethanone (88%), $^1$H NMR (400 MHz, CDCl$_3$) δ 7.87 (d, 2H, J=8.8 Hz), 7.48 (d, 1H, J=1.8 Hz), 7.46 (s, 1H), 7.39 (dd, 1H, J=9.0, 6.8 Hz), 6.80 (d, 2H, J=8.8 Hz), 4.98 (s, 2H), 3.21 (sept, 1H, J=7.0

Hz), 2.53 (s, 3H), 1.45 (d, 6H, J=7.0 Hz); Preparation 31B: 1-{4-[3-(2,6-Dichloro-phenyl)-5-isopropyl-3H-[1,2,3]triazol-4-ylmethoxy]-3-methyl-phenyl}-ethanone (89%), $^1$H NMR (400 MHz, CDCl$_3$) δ 7.75 (dd, 1H, J=8.5, 0.1 Hz), 7.72 (d, 1H, J=1.9 Hz), 7.49 (d, 1H, J=1.8 Hz), 7.47 (s, 1H), 7.42 (dd, 1H, J=9.2, 6.6 Hz), 6.78 (d, 1H, J=8.8 Hz), 4.99 (s, 2H), 3.22 (sept, 1H, J=7.0 Hz), 2.52 (s, 3H), 2.06 (s, 3H), 1.46 (d, 6H, J=7.0 Hz); Preparation 31C: 4'-[3-(2,6-Dichloro-phenyl)-5-isopropyl-3H-[1,2,3]triazol-4-ylmethoxy]-biphenyl-4-carbonitrile, ES/MS m/e (35Cl) 463 (M+1).

Preparation 32

2-{4-[3-(2,6-Dichloro-phenyl)-5-isopropyl-3H-[1,2,3]triazol-4-ylmethoxy]-2-methyl-phenyl}-propan-2-ol To a −78° C. solution of 1-{4-[3-(2,6-Dichloro-phenyl)-5-isopropyl-3H-[1,2,3]triazol-4-ylmethoxy]-2-methyl-phenyl}-ethanone (500 mg, 1.19 mmol) in THF (12 mL) is added methylmagnesium bromide (2.0 mL, 5.98 mmol, 3.0 M in THF) dropwise. The reaction mixture is warmed to room temperature. After 4 h, the reaction is cooled to 0° C., quenched with NH$_4$Cl, and warmed to room temperature. The reaction mixture is concentrated and the residue is partitioned between Et$_2$O and 1N HCl. The aqueous layer is extracted with Et$_2$O and the combined organic layers are washed with brine, dried (MgSO$_4$), filtered, concentrated and chromatographed eluting with 0% to 30% EtOAC/Hexane to yield the title compound (414 mg, 80%). $^1$H NMR (400 MHz, CDCl$_3$) δ 7.49-7.46 (m, 2H), 7.43-7.38 (m, 1H), 7.23-7.19 (m, 2H), 6.70 (d, 1H, J=8.8 Hz), 4.89 (s, 2H), 3.20 (sept, 1H, J=6.6 Hz), 2.04 (s, 3H), 1.53 (s, 6H), 1.45 (d, 6H, J=6.6 Hz).

The following list of compounds is prepared essentially according to the preparation of 2-{4-[3-(2,6-Dichloro-phenyl)-5-isopropyl-3H-[1,2,3]triazol-4-ylmethoxy]-2-methyl-phenyl}-propan-2-ol using the appropriate starting material. Preparation 32A: 2-{4-[3-(2,6-Dichloro-phenyl)-5-isopropyl-3H-[1,2,3]triazol-4-ylmethoxy]-phenyl}-propan-2-ol (63%), $^1$H NMR (400 MHz, CDCl$_3$) δ 7.48 (d, 1H, J=1.3 Hz), 7.46 (s, 1H), 7.39 (dd, 1H, J=9.2, 7.0 Hz), 7.35 (d, 2H, J=8.8 Hz), 6.73 (d, 2H, J=8.8 Hz), 4.90 (s, 2H), 3.19 (sept, 1H, J=7.0 Hz), 1.54 (s, 6H), 1.44 (d, 6H, J=7.0 Hz); Preparation 32B: 2-{4-[3-(2,6-Dichloro-phenyl)-5-isopropyl-3H-[1,2,3]triazol-4-ylmethoxy]-3-methyl-phenyl}-propan-2-ol (58%), $^1$H NMR (400 MHz, CDCl$_3$) δ 7.48 (d, 1H, J=1.8 Hz), 7.46 (s, 1H), 7.40 (dd, 1H, J=9.2, 6.6 Hz), 7.23-7.19 (m, 2H), 6.70 (d, 1H, J=8.8 Hz), 4.89 (s, 2H), 3.21 (sept, 1H, J=7.0 Hz), 2.04 (s, 3H), 1.54 (s, 6H), 1.45 (d, 6H, J=7.0 Hz).

Preparation 33

4-Formyl-2-methyl-benzoic acid methyl ester

Step A

To a solution of 4-iodo-3-methyl-benzoic acid (5.2 g, 20 mmol) in THF (30 mL), is added 2.0 M borane-dimethyl sulfide complex in THF (40.0 mL, 80 mmol) dropwise. The reaction mixture is stirred overnight. The reaction mixture is quenched carefully at 0° C. with methanol (20 mL) and the mixture is evaporated to dryness under reduced pressure. The residue is partitioned between EtOAc (80 mL) and water (60 mL). The organic phase is washed with brine (60 mL), dried (Na$_2$SO$_4$), filtered, and concentrated under reduced pressure to a residue. The residue is purified by flash chromatography (AnaLogix, gradient EtOAc/Hexane) to give (4-Iodo-3-methyl-phenyl)-methanol as white solid (4.7 g, 95%). $^1$HNMR (CDCl$_3$) (ppm): 2.4 (3H, s), 4.55 (2H, s), 6.8-7.75 (3H, m).

Step B

To a 50 mL hastalloy Parr pressure reactor is charged palladium acetate (0.161 g, 0.7 mmol, 1,4 bis-(diphenylphosphino)butane (DPPB) (0.363 g, 0.85 mmol), (4-Iodo-3-methyl-phenyl)-methanol (1.80 g, 7.25 mmol), dry methanol (10.0 ml), dry triethylamine (5.25 ml, 37.7 mmol) and dry acetonitrile (15.0 ml). The reaction vessel is evacuated and filled with nitrogen (4×). Next the reaction vessel is evacuated and filled with carbon monoxide (4×). The reaction vessel is pressurized with carbon monoxide (100 psig, 690 KPa), sealed, and agitated at 100° C. for 4 hours while the carbon monoxide pressure is maintained at 100 psig. The reaction is cooled to ambient temperature and the carbon monoxide is vented from the reaction vessel. After filtration, the filtrate is concentrated to a residue. The residue is partitioned between EtOAc (50 mL) and water (50 mL). The organic phase is washed with brine (50 mL), dried (Na$_2$SO$_4$), filtered, and concentrated under reduced pressure to a residue. The residue is purified by flash chromatography to give 4-hydroxymethyl-2-methyl-benzoic acid methyl ester as syrup (1.18 g, 90%). LC-MS: 181.3 (M+1).

Step C

To a 0° C. solution of 4-hydroxymethyl-2-methyl-benzoic acid methyl ester (0.49 g, 2.7 mmol) in methylene chloride (8.0 mL) is added sodium bicarbonate (0.46 g, 5.4 mmol) and Dess-Martin periodinane (0.14 g, 3.3 mmol) sequentially. The reaction mixture is stirred at room temperature for 1.0 h and quenched with water (2.0 mL). The mixture is partitioned between CH$_2$Cl$_2$ (30 mL) and water (30 mL). The organic phase is washed with brine (30 mL), dried (Na$_2$SO$_4$), filtered, and concentrated under reduced pressure to a residue. The residue is purified by flash chromatography to give the title compound as syrup (0.35 g, 72%). $^1$HNMR (CDCl$_3$) (ppm): 2.6 (3H, s), 3.85 (3H, s), 7.65-8.0 (3H, m), 10.0 (1H, s).

The title compound is prepared essentially as described in the synthesis of 4-formyl-2-methyl-benzoic acid methyl ester using the appropriate starting material. Preparation 33A: 4-Formyl-2-trifluoromethyl-benzoic acid methyl ester (1.29 g, 92%), LC-ES/MS m/e 233.3 (M+1).

Preparation 34

4-Formyl-2-methyl-benzoic acid methyl ester

To a 1 L Parr autoclave under N$_2$ atmosphere is charged palladium (II) acetate (2.19 g, 0.0097 mol) and butyl-1-diadamantylphosphine (10.42 g, 0.291 mol) in toluene (100 mL). To this mixture are added (4-bromo-2-methyl-benzoic acid methyl ester (222 g, 0.969 mol), tetramethylethylenediamine (97.1 mL, 0.63 equiv), and toluene (325 mL). The autoclave is sealed and removed from N$_2$ atmosphere. To the autoclave is placed a constant pressure of SynGas® (equal CO/H$_2$ mix, 75 psi). The reaction is stirred for 18 h at 85° C. The crude reaction mixture is filtered through a diatomaceous earth pad and washed with CH$_2$Cl$_2$ until clear. The solvent is removed under reduced pressure to produce a red oil (86%) that crystallizes upon standing. $^1$H NMR (400 MHz, CDCl$_3$) δ 10.0 (s, 1H), 7.9 (d, 1H), 7.78 (m, 2H), 3.81 (s, 3H), 2.57 (s, 3H).

Preparation 35

2-Butoxy-4-formyl-benzoic acid methyl ester

Step A

To a 0° C. mixture of 2-hydroxy-4-methyl-benzoic acid methyl ester (1.0 g, 6.0 mmol), triphenylphosphine (1.9 g, 7.2 mmol), and n-butanol (0.89 g, 12.0 mmol) in THF (10.0 mL) is added DIAD (1.45 g, 7.2 mmol) dropwise. The mixture is stirred at room temperature overnight. The mixture is evaporated to dryness under reduced pressure. The residue is partitioned between EtOAc (50 mL) and water (50 mL). The organic phase is washed with brine (50 mL), dried ($Na_2SO_4$), filtered, and concentrated under reduced pressure to a residue. The residue is purified by flash chromatography to give 2-Butoxy-4-methyl-benzoic acid methyl ester as a syrup (1.0 g, 74%). LC-MS: 223.3 (M+1).

Step B

A mixture of 2-butoxy-4-methyl-benzoic acid methyl ester (0.85 g, 3.8 mmol), dibenzoyl peroxide (100 mg), and NBS (0.68 g, 3.8 mmol) in $CCl_4$ (20 mL) is heated to 70° C. overnight. The solid is filtered off and the filtrate is concentrated to a residue. The residue is purified by flash chromatography to give 4-Bromomethyl-2-butoxy-benzoic acid methyl ester as a syrup (0.6 g, 52%). LC-MS: 301.0 (M+1).

Step C

A mixture of 4-bromomethyl-2-butoxy-benzoic acid methyl ester (0.0500 g, 1.67 mmol), THF (10 mL), $H_2O$ (10 mL), and LiOH (0.0160 g, 6.68 mmol) is stirred at 50° C. overnight. The mixture is acidified with 1.0 M HCl and the product is extracted with EtOAc (40 mL). The organic phase is washed with brine (20 mL) and dried ($Na_2SO_4$). After filtration, the filtrate is concentrated under reduced pressure to a residue. The residue is dissolved in $CH_2Cl_2$ (10 mL) and MeOH (10 mL) and treated with 2.0 M $TMSCHN_2$ in hexane (5.0 mL, 10 mmol) at room temperature for 30 minutes. After concentration the residue is purified by flash chromatography to give 2-Butoxy-4-hydroxymethyl-benzoic acid methyl ester as a syrup (270 mg, 68%). LC-ES/MS: 239.3 (M+1).

Step D

To a 0° C. solution of 2-butoxy-4-hydroxymethyl-benzoic acid methyl ester (0.270 g, 1.13 mmol) in methylene chloride (10 mL) are added sodium bicarbonate (0.14 g, 1.7 mmol) and Dess-Martin periodinane (0.58 g, 1.4 mmol) sequentially. The reaction mixture is stirred at room temperature for 1.0 h and quenched with water (10 mL). The reaction mixture is partitioned between $CH_2Cl_2$ (30 mL) and water (20 mL). The organic phase is washed with brine (20 mL), dried ($Na_2SO_4$), filtered, and concentrated under reduced pressure to a residue. The residue is purified by flash chromatography to give the title compound as a syrup (240 mg, 90%). LC-ES/MS: 237.3 (M+1).

Preparation 36

[4-(tert-Butyl-dimethyl-silanyloxy)-2-methyl-phenyl]-methyl-amine

Step A

To a suspension of 4-amino-3-methyl-phenol (10.8 g, 88 mmol) in THF (80 mL) and sat. sodium bicarbonate (50 mL) is added benzyl chloroformate (18.0 g, 105 mmol) dropwise. The reaction mixture is stirred for 1.0 h. The two phases are separated and the organic phase is concentrated to a residue. The residue is partitioned between EtOAc (100 mL) and 5% HCl (50 mL). The organic phase is washed with brine (100 mL), dried ($Na_2SO_4$), filtered, and concentrated under reduced pressure to a residue. The residue is purified by flash chromatography to give (4-Hydroxy-2-methyl)-carbamic acid benzyl ester as brown solid (21.0 g, 93%). LC-ES/MS: 258.3 (M+1), 256.0 (M−1).

Step B

To a 0° C. solution of (4-hydroxy-2-methyl)-carbamic acid benzyl ester (21.0 g, 81.7 mmol) and imidazole (6.7 g, 98 mmol) in DMF (100 ml) is added a solution of tert-butyldimethylsilyl chloride (14.8 g, 98 mmol) in DMF (20 mL). After the addition, the mixture is stirred at room temperature for 30 minutes. The solvent is removed under reduced pressure to give a residue, which is partitioned between EtOAc (100 mL) and 5% HCl (50 mL). The organic phase is washed with brine (100 mL), dried ($Na_2SO_4$), filtered, and concentrated under reduced pressure to a residue. The residue is purified by flash chromatography to give [4-(tert-Butyl-dimethyl-silanyloxy)-2-methyl-phenyl]-carbamic acid benzyl ester as yellowish solid (28.8 g, 95%). LC-ES/MS: 372.3 (M+1).

Step C

To a 0° C. solution of [4-(tert-butyl-dimethyl-silanyloxy)-2-methyl-phenyl]-carbamic acid benzyl ester (18 g, 48.5 mmol) in DMF (100 mL) is added sodium hydride (60% dispersion in oil, 2.3 g, 58 mmol) portionwise. The reaction mixture is stirred at room temperature for 30 minutes, followed by the addition of iodomethane (8.2 g, 58 mmol). The mixture is stirred at room temperature overnight. The solvent is removed under reduced pressure to give a residue, which is partitioned between EtOAc (100 mL) and water (100 mL). The organic phase is washed with brine (100 mL), dried ($Na_2SO_4$), filtered, and concentrated under reduced pressure to a residue. The residue is purified by flash chromatography to give [4-(tert-Butyl-dimethyl-silanyloxy)-2-methyl-phenyl]-methyl-carbamic acid benzyl ester as oil (14.0 g, 75%). LC-ES/MS: 386.0 (M+1).

Step D

The mixture of [4-(tert-butyl-dimethyl-silanyloxy)-2-methyl-phenyl]-methyl-carbamic acid benzyl ester (14.0 g, 36.0 mmol) and palladium on carbon (10 wt %, 0.5 g) in methanol (100.0 mL) is stirred under a hydrogen atmosphere (balloon) at room temperature overnight. After filtration the filtrate is concentrated under reduced pressure to a residue. The residue is purified by flash chromatography to give the title compound as oil (7.4 g, 81%). LC-ES/MS: 252.3 (M+1).

Preparation 37

4-({[4-(tert-Butyl-dimethyl-silanyloxy)-2-methyl-phenyl]-methyl-amino}-methyl-2-methyl-benzoic acid methyl ester To a solution of [4-(tert-butyl-dimethyl-silanyloxy)-2-methyl-phenyl]-methyl-amine (0.64 g, 2.6 mmol) and 4-formyl-2-methyl-benzoic acid methyl ester (0.38 g, 2.1 mmol), acetic acid (0.25 g, 4.2 mmol) in 1,2-dichloroethane (10.0 mL) is added sodium triacetoxyborohydride (0.89 g, 4.2 mmol) in portions. The mixture is stirred at room temperature overnight. The reaction is quenched with 5% aq. sodium bicarbonate (5 mL) and is partitioned between EtOAc (60 mL) and water (50 mL). The organic layer is washed with brine (50 mL), dried (Na$_2$SO$_4$), filtered, and concentrated. The residue is purified by flash column chromatography to afford the title compound as a syrup (1.0 g, 95%). LC-ES/MS m/e 414.3 (M+1).

Preparation 38

2-Butoxy-4-({[4-(tert-butyl-dimethyl-silanyloxy)-2-methyl-phenyl]-methyl-amino}-methyl)-benzoic acid methyl ester The title compound is prepared by reductive amination of [4-(tert-butyl-dimethyl-silanyloxy)-2-methyl-phenyl]-methyl-amine with 2-butoxy-4-formyl-benzoic acid methyl ester, essentially as described in the synthesis of 4-({[4-(tert-butyl-dimethyl-silanyloxy)-2-methyl-phenyl]-methyl-amino}-methyl)-2-methyl-benzoic acid methyl ester using the appropriate starting material. The title compound is obtained as syrup after workup. LC-ES/MS m/e 472.3 (M+1).

Preparation 39

4-{[(4-Hydroxy-2-methyl-phenyl)-methyl-amino]-methyl}-2-methyl-benzoic acid methyl ester To a solution of 4-({[4-(tert-butyl-dimethyl-silanyloxy)-2-methyl-phenyl]-methyl-amino}-methyl)-2-methyl-benzoic acid methyl ester (1.0 g, 2.1 mmol) in THF (20.0 mL) is added 1.0 M TBAF/THF (3.2 mL, 3.2 mmol) at room temperature. The reaction mixture is stirred for 1.0 h. The reaction mixture is partitioned between EtOAc (30 mL) and water (30 mL). The organic phase is washed with brine (30 mL), dried (Na$_2$SO$_4$), filtered, and concentrated under reduced pressure to a residue. The residue is purified by flash chromatography to give the title compound as oil (0.45 g, 62%). LC-ES/MS: 300.3 (M+1), 298.3 (M−1).

Preparation 40

2-Butoxy-4-{[(4-hydroxy-2-methyl-phenyl)-methyl-amino]-methyl}-benzoic acid methyl ester The title compound (200 mg, 55%) is prepared essentially as described in the synthesis of 4-{[(4-hydroxy-2-methyl-phenyl)-methyl-amino]-methyl}-2-methyl-benzoic acid methyl ester using the appropriate starting material. LC-ES/MS: 358.3 (M+1).

Preparation 41

3-(2,6-Dichloro-phenyl)-5-trifluoromethyl-3H-[1,2,3]triazole-4-carboxylic acid ethyl ester A mixture of 2-Azido-1,3-dichloro-benzene (25.0 g, 132.9 mmol) and 4,4,4-trifluoro-but-2-ynoic acid ethyl ester (26.5 g, 159.6 mmol) in toluene (30 mL) are heated at 80° C. for 18 h. A large exotherm is observed at 25 minutes. The reaction is removed from heat until exotherm subsides. Two regioisomers are observed in a range of 1:1 to 3:1 in favor of the desired product. The reaction mixture is concentrated under reduced pressure to 51 g of crude material and purified via column chromatography using a gradient of 35-60% DCM in Hexanes to yield the title compound (28 g, 59%). ES/MS m/e 353.0 (M+1).

The following compound is prepared essentially according to the preparation of 3-(2,6-Dichloro-phenyl)-5-trifluoromethyl-3H-[1,2,3]triazole-4-carboxylic acid ethyl ester using the appropriate starting material.

Preparation 41A: 3-(2-Trifluoromethoxy-phenyl)-5-trifluoromethyl-3H-[1,2,3]triazole-4-carboxylic acid ethyl ester (42%), ES/MS m/e 370.0 (M+1).

Preparation 42

[3-(2,6-Dichloro-phenyl)-5-trifluoromethyl-3H-[1,2,3]triazol-4-yl]methanol

To a 0° C. solution of 3-(2,6-dichloro-phenyl)-5-trifluoromethyl-3H-[1,2,3]triazole-4-carboxylic acid ethyl ester (28 g, 79 mmol) in THF (200 mL) is added dropwise 1M DIBAL (166 mL, 166 mmol) keeping the temperature below 5° C. After the addition, the bath is removed and the reaction is stirred for 18 h. The reaction is cooled to 0° C. and ether (300 mL) is added. The reaction is quenched with 1N HCl (250 mL) dropwise keeping the temperature below 15° C. The layers are separated and the water layer is washed with Ether (100 mL). The organics are combined and washed with water, brine, and dried with Na$_2$SO$_4$. The organic layer is concentrated to dryness to yield the title compound (24 g, 97%) and is used with no further purification. ES/MS m/e 312.0 (M+1).

The following compound is prepared essentially according to the preparation of [3-(2,6-Dichloro-phenyl)-5-trifluoromethyl-3H-[1,2,3]triazol-4-yl]methanol using the appropriate starting material.

Preparation 42A: [3-(2-Trifluoromethoxy-phenyl)-5-trifluoromethyl-3H-[1,2,3]triazol-4-yl]methanol (95%), ES/MS m/e 328.0 (M+1).

Preparation 43

4-Iodo-3-trifluoromethyl-benzoic acid

4-Amino-3-trifluoromethyl benzoic acid (1.8 g, 8.8 mmol) is suspended in conc. HCl (30 mL). A solution of sodium nitrite (0.76 g, 11.0 mmol) in water (15 mL) is added dropwise at 0° C. The mixture is stirred at 0-10° C. for 30 min. A solution of potassium iodide (14.6 g, 88 mmol) in water (25 mL) is added dropwise. The mixture is stirred at room temperature for 1 h. The product is extracted with EtOAc (80 mL), washed with brine (80 mL), dried (Na$_2$SO$_4$), filtered, and concentrated under reduced pressure to a residue. The residue is purified by flash chromatography using a gradient (EtOAc/Hexane) to afford the title compound (2.4 g, 86%) as a solid. LC-ES/MS m/e 339.3 (M+23), 315.0 (M−1).

Preparation 44

6-Bromo-benzo[d]isothiazole-3-carboxylic acid

The title compound is prepared essentially according to Procedure 3 in WO 2005/092890. ES/MS m/e 255.0 (M−1).

Preparation 45

6-(4-Hydroxy-2-methyl-phenyl)-benzo[d]isothiazole-3-carboxylic acid

To a degassed solution of 6-Bromo-benzo[d]isothiazole-3-carboxylic acid (0.42 g, 1.54 mmol), 3-Methyl-4-(4,4,5,5- tetramethyl-[1,3,2]dioxaborolan-2-yl-phenol (0.54, 2.31 mmol), 2-Dicyclohexylphosphino-2',6'-dimethoxy-1,1'-biphenyl (0.064 g, 0.154 mmol), and potassium phosphate (0.71 g, 3.1 mmol) in dioxane (8 mL) and water (4 mL) is added Pd(OAc)$_2$ (6.5 mg, 0.03 mmol). The reaction is degassed again and heated to 80 degrees for 18 h. The reaction is cooled to room temperature and concentrated under reduced pressure. The material is diluted with EtOAc and 1N HCl. The layers are separated and concentrated under reduced pressure. The crude material is diluted with 20 mL of MeOH and 2 mL H$_2$SO$_4$ and heated to reflux for 2 h. The reaction is concentrated onto silica and purified using a gradient of 20 to 50% EtOAc in Hexanes to yield the title compound (0.12 g, 26% yield). ES/MS m/e 300.0 (M+1).

Preparation 46

6-Bromo-1H-indazole-3-carboxylic acid methyl ester

The title compound is prepared from 6-Bromo-1H-indole-2,3-dione essentially as described in procedure 4 of WO2005092890. ES/MS m/e 254.0 (M+1).

Preparation 47

6-Bromo-1-isopropyl-1H-indazole-3-carboxylic acid methyl ester

The title compound is prepared essentially as described in procedure 1d WO2005/080389 substituting 6-Bromo-1H-indazole-3-carboxylic acid methyl ester for 1H-indazole-3-carboxylic acid methyl ester. ES/MS m/e 296.0 (M+1).

Preparation 48

6-Bromo-1-methyl-1H-indazole-3-carboxylic acid methyl ester

The title compound is prepared essentially as described in the synthesis of 6-bromo-1-isopropyl-1H-indazole-3-carboxylic acid substituting 6-bromo-1H-indazole-3-carboxylic acid methyl ester for 1H-indazole-3-carboxylic acid methyl ester and methyl iodide for isopropyl iodide ES/MS m/e 268.0 (M+1).

Preparation 49

6-(4-Hydroxy-2-methyl-phenyl)-1-methyl-1H-indazole-3-carboxylic acid

To a degassed solution of 6-bromo-1-methyl-1H-indazole-3-carboxylic acid methyl ester (0.61 g, 2.4 mmol), 3-methyl-4-(4,4,5,5-tetramethyl-[1,3,2]dioxaborolan-2-yl-phenol (0.84, 3.6 mmol), 2-dicyclohexylphosphino-2',6'-dimethoxy-1,1'-biphenyl (0.098 g, 0.240 mmol), and potassium phosphate (1.0 g, 4.8 mmol) in dioxane (10 mL) and water (5 mL) is degassed and treated with Pd(OAc)$_2$ (27 mg, 0.12 mmol). The reaction is degassed again and heated to 90° C. for 18 h. The reaction is cooled to room temperature, concentrated onto silica gel under reduced pressure, and purified via flash chromatography using a gradient of 10% to 30% EtOAc in Hexanes to yield the title compound (0.53 g, 75%). ES/MS m/e 297.0 (M+1).

Preparation 50

6-(4-Hydroxy-2-methyl-phenyl)-1-isopropyl-1H-indazole-3-carboxylic acid methyl ester The title compound (2.88 g, 98%) is prepared essentially according to the synthesis of 6-(4-hydroxy-2-methyl-phenyl)-1-methyl-1H-indazole-3-carboxylic acid except using a gradient of 20% to 60% EtOAc in Hexanes in the final purification. ES/MS m/e 325.0 (M+1).

Preparation 51

4-Amino-3-fluoro-phenol

A mixture of 3-fluoro-4-nitrophenol (2.20 g, 14.0 mmol) in 25 mL ethyl acetate is evacuated under reduced pressure and filled with nitrogen three times. Palladium, 10% by weight on carbon (220 mg) is added. The mixture is evacuated under reduced pressure and filled with nitrogen three times. The mixture is evacuated under reduced pressure and filled with hydrogen. The mixture is stirred under hydrogen atmosphere (balloon) over night. The mixture is then filtered over diatomaceous earth and concentrated to provide the title compound (1.7 g, 96%) as a brown solid. $^1$H NMR (400 MHz, DMF-d$_7$) δ 8.75 (s, 1H), 6.78 (m, 1H), 6.40 (m, 1H), 6.50 (m, 1H), 4.38 (s, 2H).

Preparation 52

4-[(2-Fluoro-4-hydroxy-phenylamino)-methyl]-2-methyl-benzoic acid methyl ester

A mixture of 4-amino-3-fluoro-phenol (900 mg, 7.08 mmol) and 4-formyl-2-methyl-benzoic acid methyl ester (1.23 g, 6.90 mmol) in 35 mL acetic acid is stirred for two hours at room temperature. Sodium triacetoxyborohydride (3.20 g, 15.1 mmol) is added and stirred at room temperature. Upon completion, the mixture is concentrated under reduced pressure and partitioned between ethyl acetate and saturated aqueous sodium bicarbonate. The aqueous layer is separated and extracted with ethyl acetate (3×). The combined ethyl acetate layers are dried (MgSO$_4$) and concentrated under reduced pressure. The residue is purified on 120 g silica eluting with a gradient of ethyl acetate in heptane (10% to 60%) to provide the title compound (1.9 g, 93%) as a yellow oil. ES/MS m/e 290.0 (M+1).

Preparation 53

4-{[(2-Fluoro-4-hydroxy-phenyl)-methyl-amino]-methyl}-2-methyl-benzoic acid methyl ester A mixture of 4-[(2-fluoro-4-hydroxy-phenylamino)-methyl]-2-methyl-benzoic acid methyl ester (1.89 g, 6.53 mmol) and 37% formaldehyde (2.0 mL) in acetic acid (20 mL) is stirred for 40 minutes. Sodium triacetoxyborohydride (2.80 g, 13.2 mmol) is added and stirred at room temperature. Upon completion of the reaction, the mixture is concentrated and partitioned between ethyl acetate and saturated aqueous sodium bicarbonate. The aqueous layer is separated and extracted with ethyl acetate (3×). The combined ethyl acetate layers are dried (MgSO$_4$) and concentrated under reduced pressure. The residue is purified on 120 g silica eluting with a gradient of ethyl acetate in heptane (10% to 60%) to provide the titled compound (1.0 g, 51%) as a white solid. LC-ES/MS m/e 304.0 (M+1).

Preparation 54

Ethyl 4,4,4-trifluoro-2-(triphenylphosphoranylidene)acetoacetate

To a 2° C. suspension of (carbethoxymethyl) triphenylphosphonium bromide (1000 g, 2.28 mol) in 5 L of THF under nitrogen is added triethylamine (642 mL, 4.57 mol). After the mixture is stirred for 30 minutes at 2° C., trifluoroacetic acid anhydride (357 mL, 2.51 mol) is added via addition funnel over 40 minutes. The mixture is allowed to stir for 2 hours and the precipitate is filtered off. The filtrate liquids are concentrated under reduced pressure to afford a yellow oily residue. The residue is triturated with water (3 L) to afford a crystalline solid that is collected by filtration. The solid is washed with water and dried under vacuum overnight. The solid is recrystallized from MeOH-water to give the title compound as a white solid (770 g, 76%). ES/MS m/e 446 (M+1).

Preparation 55

4,4,4-Trifluoro-2-butynoic acid ethyl ester

A mixture of ethyl 4,4,4-trifluoro-2-(triphenylphosphoranylidene)acetoacetate (270 g, 617 mmol) and potassium carbonate (54 g, 490 mmol) is heated from 160° C. to 225° C. in 3 h at 2-3 mbar vacuum. The title compound is distilled and recovered in a cold trap to yield the title compound (85 g, 83%) as a slightly yellow oil. ES/MS m/e 167 (M+1).

Preparation 56

4-Bromo-2-methylbenzoic acid methyl ester

Acetyl chloride (199 mL, 2.79 mol) is added to a solution of 4-bromo-2-methylbenzoic acid (500 g, 2.32 mol) in methanol (2500 mL) at 5° C. The mixture is heated at 65° C. for 7 hours. The mixture is cooled to room temperature and sodium carbonate (19 g, 0.18 mol) is added. The reaction mixture is stirred for 15 minutes. The slurry is filtered and the filtrate is concentrated under reduced pressure. The resulting residue is partitioned between MTBE (400 mL) and water (400 mL). The organic phase is washed with brine, dried over magnesium sulfate, and concentrated to give the title compound (520 g) as a golden oil. ES/MS m/e 216 (M+1).

Preparation 57

4-formyl-2-methyl-benzoic acid, methyl ester

A mixture of 4-bromo-2-methylbenzoic acid methyl ester (513 g, 2.24 mol), tetramethylethylenediamine (209 mL, 1.39 mol), palladium acetate (5 g), cataCXium A® (23 g) and toluene (3000 mL) is charged into a reactor. The reactor is pressurized with SynGas® (100 psi). The mixture is heated to 85° C. and held under SynGas® (100 psi) overnight. After 18 h, the reaction is cooled to room temperature, filtered through a pad of diatomaceous earth, and concentrated to an oil. The residue is triturated with heptane to afford the title compound as a yellow solid that is filtered and washed with heptane (350 g, 88% yield). ES/MS m/e 179 (M+1).

Preparation 58

4-((4-Hydroxy-2-methylphenylamino)methyl)-2-methyl benzoic acid, methyl ester 4-Amino-m-cresol (242 g, 1.96 mol) is added to a slurry of 4-formyl-2-methyl-benzoic acid, methyl ester (350 g, 1.96 mol) and acetic acid (3100 mL) at room temperature. Sodium triacetoxyborohydride (728 g, 3.44 mol) is added portionwise, keeping the temperature below 30° C. using an ice water bath. After overnight stirring, the reaction mixture is concentrated under reduced pressure. The residue is adjusted to pH 5 using aqueous saturated sodium bicarbonate. The resulting solid is filtered off, washed with water, and dried under vacuum overnight to give the title compound (460 g, 82%) as a brown powder. ES/MS m/e 179 (M+1).

Preparation 59

4-{[(4-hydroxy-2-methylphenyl)methylamino]methyl}-2-methyl benzoic acid, methyl ester Formic acid (165 mL, 4.37 ml) is added dropwise to a slurry of 4-((4-hydroxy-2-methylphenylamino)methyl)-2-methyl benzoic acid methyl ester (250 g, 0.88 mol) and formaldehyde (435 mL, 37% in aqueous) at room temperature. The reaction is stirred overnight. To the reaction mixture is added 1M HCl (600 mL) and the mixture is extracted with MTBE. The aqueous phase is adjusted to pH 8 with 6M NaOH and extracted with MTBE (2×1000 mL). The combined organic layers are combined, dried over magnesium sulfate, filtered, and concentrated under reduced pressure. The residue is purified using a plug of silica gel eluting with 10% EtOAc/hexanes to give the title compound (127 g, 48%) as a white solid. ES/MS m/e 300 (M+1).

Preparation 60

5-Bromomethyl-1-(2,6-dichlorophenyl)-4-trifluoromethyl-1H-[1,2,3]-triazole

Triphenylphosphine (16.4 g, 62.5 mmol) is added to a suspension of [3-(2,6-dichlorophenyl)-5-trifluoromethyl-3H-[1,2,3]triazol-4-yl]-methanol (13 g, 41.69 mmol) in dichlormethane (80 mL). The mixture is cooled to 0° C. and carbon tetrabromide (20.7 g, 62.5 mmol) is added. The reaction is stirred at room temperature for 1.5 hours. The solvent is evaporated under reduced pressure and the residue is purified by flash chromatography eluting with hexanes/EtOAc (95:5 to 8:2) to obtain the title compound (15.6 g, 96% yield). ES/MS m/e 374 (M+1).

Examples

Example 1

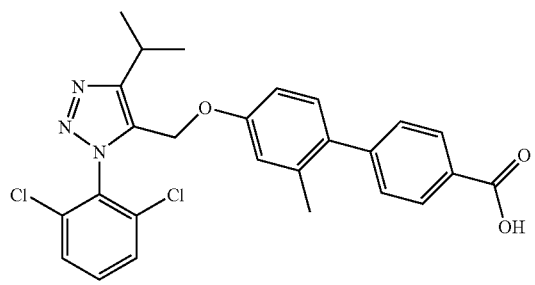

4'-[3-(2,6-Dichloro-phenyl)-5-isopropyl-3H-[1,2,3]triazol-4-ylmethoxy]-2'-methyl-biphenyl-4-carboxylic acid Step A To a solution of 5-chloromethyl-1-(2,6-dichloro-phenyl)-4-isopropyl-1H-[1,2,3]triazole (0.1 g, 0.328 mmol) in dimethylformamide (3 mL) is added 4'-hydroxy-2'methyl-biphenyl-4-carboxylic acid methyl ester (0.079 g, 0.326 mmol) and cesium carbonate (0.21 g, 0.646 mmol). The reaction is heated to 55° C. for 2.5 h and is cooled to room temperature. The reaction mixture is concentrated under reduced pressure. The residue is dissolved in 1N hydrochloric acid and ethyl acetate. The layers are separated and the aqueous is extracted again with ethyl acetate. The organic layers are combined and are washed with brine, dried over sodium sulfate, filtered, and concentrated under reduced pressure to give 4'-[3-(2,6-dichloro-phenyl)-5-isopropyl-3H-[1,2,3]triazol-4-ylmethoxy]-2'-methyl-biphenyl-4-carboxylic acid methyl ester. ES/MS m/e ($^{35}$Cl/$^{37}$Cl) 510.2/512.2 (M+1).

Step B

A solution of 4'-[3-(2,6-dichloro-phenyl)-5-isopropyl-3H-[1,2,3]triazol-4-ylmethoxy]-2'-methyl-biphenyl-4-carboxylic acid methyl ester (4.55 g, 1 equiv) and 1N NaOH (44.6 mL, 5 equiv) in MeOH (200 mL) is heated to 75° C. for 1 h. The reaction mixture is cooled to room temperature and is concentrated under reduced pressure. The residue is dissolved in water (200 mL) and the solution is acidified with 5N HCl. The resulting precipitate is filtered and dried under reduced pressure to give the title compound (4.21 g, 95%). ES/MS m/e ($^{35}$Cl/$^{37}$Cl) 496.3/498 (M+1).

The following compounds in Table 1 are prepared essentially according to the preparation of 4'-[3-(2,6-Dichloro-phenyl)-5-isopropyl-3H-[1,2,3]triazol-4-ylmethoxy]-2'-methyl-biphenyl-4-carboxylic acid using the appropriate starting material.

Example 12

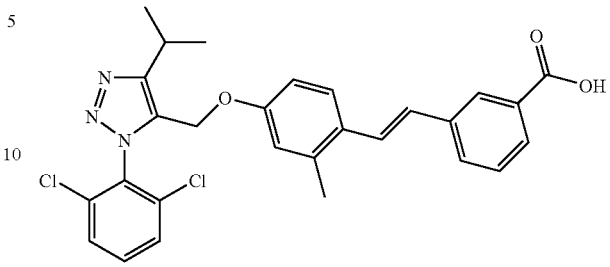

3-(2-(4-(3-(2,6-Dichloro-phenyl)-5-isopropyl-3-H-(1,2,3)triazol-4ylmethyoxy)-2-methyl-phenyl)-vinyl)-benzoic acid Step A To a solution of 3-(2-(4-hydroxy-2-methyl-phenyl)-vinyl)-benzoic acid methyl ester (0.09 4 g, 0.351 mmol) and (3-(2,6-dichloro-phenyl)-5-isopropyl-3H-(1,2,3)triazol-4-yl)-methanol (0.100 g, 0.351 mmol) in THF (3 mL) are added triphenylphosphine (0.184 g, 0.702 mmol) and diethyl azodicarboxylate (0.120 g, 0.720 mmol). The reaction is stirred overnight. The reaction is partitioned between ether and water. The organic layer is washed with brine and dried over sodium sulfate. The organic layers are filtered and concentrated. The crude solid is purified via flash chromatography using hexane:ethyl acetate (2:1) as eluent to give 3-(2-(4-(3-(2,6-Dichloro-phenyl)-5-isopropyl-3-H-(1,2,3)triazol-4ylmethyoxy)-2-methyl-phenyl)-vinyl)-benzoic acid methyl ester (0.04 g). ES/MS m/e ($^{35}$Cl/$^{37}$Cl) 535.8/538.2 (M+1).

Step B

To a solution of 3-(2-(4-(3-(2,6-dichloro-phenyl)-5-isopropyl-3-H-(1,2,3)triazol-4ylmethyoxy)-2-methyl-phenyl)-

TABLE 1

| Ex | Name | Physical Data |
|---|---|---|
| 2 | 2-{4-[3-(2,6-Dichloro-phenyl)-5-isopropyl-3H-[1,2,3]triazol-4-ylmethoxy]-phenyl}-benzo[b]thiophene-6-carboxylic acid | LC-ES/MS m/e 538 (M + 1) |
| 3 | 4'-[5-Isopropyl-3-(2-trifluoromethyl-phenyl)-3H-[1,2,3]triazol-4-ylmethoxy]-2'-methyl-biphenyl-4-carboxylic acid | LC-ES/MS m/e 496 (M + 1) |
| 4 | 2'-Chloro-4'-[5-isopropyl-3-(2-trifluoromethyl-phenyl)-3H-[1,2,3]triazol-4-ylmethoxy]-biphenyl-4-carboxylic acid | LC-ES/MS m/e 516 (M + 1) |
| 5 | 4-[({4-[5-Cyclopropyl-3-(2,6-dichloro-phenyl)-3H-[1,2,3]triazol-4-ylmethoxy]-2-methyl-phenyl}-methyl-amino)-methyl]-2-methyl-benzoic acid | LC-ES/MS m/e 551 (M + 1); 549 (M − 1) |
| 7 | 3-(2-{4-[3-(2-Chloro-6-fluoro-phenyl)-5-isopropyl-3H-[1,2,3]triazol-4-ylmethoxy]-2-methyl-phenyl}-vinyl)-benzoic acid | LC-ES/MS m/e 506.0 (M + 1), |
| 8 | 3-(2-{4-[5-Isopropyl-3-(2-trifluoromethoxy-phenyl)-3H-[1,2,3]triazol-4-ylmethoxy]-2-methyl-phenyl}-vinyl)-benzoic acid | LC-ES/MS m/e 538.0 (M + 1), |
| 9 | 3-(2-{4-[5-Isopropyl-3-(2-trifluoromethyl-phenyl)-3H-[1,2,3]triazol-4-ylmethoxy]-2-methyl-phenyl}-vinyl)-benzoic acid | LC-LC-ES/MS m/e 522.2 (M + 1) |
| 10 | 5-{4-[3-(2,6-Dichloro-phenyl)-5-isopropyl-3H-[1,2,3]triazol-4-ylmethoxy]-2-methyl-phenyl}-thiophene-2-carboxylic acid | LC-MS: 502 (M + 1), 100% |
| 11 | 5-{4-[3-(2,6-Dichloro-phenyl)-5-isopropyl-3H-[1,2,3]triazol-4-ylmethoxy]-2-methyl-phenyl}-thiophene-2-carboxylic acid | LC-ES/MS m/e 502 (M + 1) | vinyl)-benzoic acid methyl ester (0.025 g, 0.046 mmol) in THF (3 mL) is added lithium hydroxide (0.005 g, 0.21 mmol). The reaction mixture is heated to 55° C. The reaction is determined to be incomplete due to the presence of starting material by TLC (1:1 hexane/ethyl acetate). An additional amount of lithium hydroxide (0.050 g) is added and the reaction is heated to 60° C. for 3 h. The reaction is quenched with aqueous 1 N HCl and is extracted with ethyl acetate. The organic layer is washed with brine, dried over sodium sulfate, filtered, and concentrated to give the title compound. ES/MS m/e 521.8 (M+1).

The following compounds in Table 2 are prepared essentially according to the preparation of 3-(2-(4-(3-(2,6-dichloro-phenyl)-5-isopropyl-3-H-(1,2,3)triazol-4ylmethyoxy)-2-methyl-phenyl)-vinyl)-benzoic acid using the appropriate starting material.

TABLE 2

| Ex | Name | Physical Data |
|---|---|---|
| 13 | 4-[({4-[5-Isopropyl-3-(2,6-dichloro-phenyl)-3H-[1,2,3]triazol-4-ylmethoxy]-2-methyl-phenyl}-methyl-amino)-methyl]-2-methyl-benzoic acid | ES/MS m/e 553 (M + 1) |
| 14 | 6-{4-[3-(2,6-Dichloro-phenyl)-5-isopropyl-3H-[1,2,3]triazol-4-ylmethoxy]-2-methyl-phenyl}-1-methyl-1H-indole-3-carboxylic acid | LC-ES/MS m/e 548.3 (M + 1) |
| 15 | 6-{4-[3-(2,6-Dichloro-phenyl)-5-isopropyl-3H-[1,2,3]triazol-4-ylmethoxy]-2-methyl-phenyl}-benzo[b]thiophene-2-carboxylic acid | LC-ES/MS m/e 567.0 (M + 1) |
| 16 | 6-{4-[5-Isopropyl-3-(2-trifluoromethoxy-phenyl)-3H-[1,2,3]triazol-4-ylmethoxy]-2-methyl-phenyl}-benzo[b]thiophene-3-carboxylic acid | LC-ES/MS m/e 568.0 (M + 1) |
| 17 | 6-{4-[5-Cyclopropyl-3-(2,6-dichloro-phenyl)-3H-[1,2,3]triazol-4-ylmethoxy]-2-methyl-phenyl}-1-isopropyl-1H-indole-3-carboxylic acid | MS/APCI m/e 576.8 (M + 1) |
| 18 | 6-{4-[5-Cyclopropyl-3-(2,6-dichloro-phenyl)-3H-[1,2,3]triazol-4-ylmethoxy]-2-methyl-phenyl}-1-methyl-1H-indole-3-carboxylic acid | MS/APCI m/e 547.0 (M) |
| 19 | 6-{4-[5-Cyclopropyl-3-(2,6-dichloro-phenyl)-3H-[1,2,3]triazol-4-ylmethoxy]-2-methyl-phenyl}-benzo[b]thiophene-3-carboxylic acid | MS/APCI m/e 550.0 (M) |
| 20 | 6-{4-[5-Cyclopropyl-3-(2-trifluoromethoxy-phenyl)-3H-[1,2,3]triazol-4-ylmethoxy]-2-methyl-phenyl}-benzo[b]thiophene-3-carboxylic acid | MS/APCI m/e 566.0 (M + 1) |
| 21 | 6-{4-[3-(2,6-Dichloro-phenyl)-5-trifluoromethyl-3H-[1,2,3]triazol-4-ylmethoxy]-2-methyl-phenyl}-1-isopropyl-1H-indole-3-carboxylic acid | LC-ES/MS m/e 603.0 (M + 1) |
| 22 | 6-{4-[5-Cyclopropyl-3-(2,6-dichloro-phenyl)-3H-[1,2,3]triazol-4-ylmethoxy]-2-methyl-phenyl}-benzo[d]isothiazole-3-carboxylic acid | LC-ES/MS m/e 549.0 (M − 1) |
| 23 | 6-{4-[5-Cyclopropyl-3-(2,6-dichloro-phenyl)-3H-[1,2,3]triazol-4-ylmethoxy]-2-methyl-phenyl}-1-methyl-1H-indazole-3-carboxylic acid | LC-ES/MS m/e 546.0 (M − 1) |
| 24 | 6-{4-[3-(2,6-Dichloro-phenyl)-5-trifluoromethyl-3H-[1,2,3]triazol-4-ylmethoxy]-2-methyl-phenyl}-1-methyl-1H-indazole-3-carboxylic acid | LC-ES/MS m/e 574.0 (M − 1) |
| 25 | 6-{4-[5-Cyclopropyl-3-(2-trifluoromethoxy-phenyl)-3H-[1,2,3]triazol-4-ylmethoxy]-2-methyl-phenyl}-1-methyl-1H-indazole-3-carboxylic acid | LC-ES/MS m/e 562.0 (M − 1) |
| 26 | 6-{4-[5-Cyclopropyl-3-(2-trifluoromethoxy-phenyl)-3H-[1,2,3]triazol-4-ylmethoxy]-2-methyl-phenyl}-1-isopropyl-1H-indazole-3-carboxylic acid | LC-ES/MS m/e 590.0 (M − 1) |
| 27 | 6-{4-[5-Cyclopropyl-3-(2,6-dichloro-phenyl)-3H-[1,2,3]triazol-4-ylmethoxy]-2-methyl-phenyl}-1-isopropyl-1H-indazole-3-carboxylic acid | LC-ES/MS m/e 574.0 (M − 1) |
| 28 | 4'-[3-(2,6-Dichloro-phenyl)-5-isopropyl-3H-[1,2,3]triazol-4-ylmethoxy]-3'-methyl-biphenyl-4-carboxylic acid | MS/APCI m/e 496 (M + 1) |
| 29 | 2'-Chloro-4'-[3-(2,6-dichloro-phenyl)-5-isopropyl-3H-[1,2,3]triazol-4-ylmethoxy]-biphenyl-4-carboxylic acid | MS/APCI m/e 516 (M + 1) |
| 30 | 4'-[3-(2,6-Dichloro-phenyl)-5-isopropyl-3H-[1,2,3]triazol-4-ylmethoxy]-2'-fluoro-biphenyl-4-carboxylic acid | MS/APCI m/e 500 (M + 1) |
| 31 | 4'-[3-(2,6-Dichloro-phenyl)-5-isopropyl-3H-[1,2,3]triazol-4-ylmethoxy]-2'-trifluoromethyl-biphenyl-4-carboxylic acid | MS/APCI m/e 550 (M + 1) |
| 32 | 4'-[3-(2,6-Dichloro-phenyl)-5-isopropyl-3H-[1,2,3]triazol-4-ylmethoxy]-2'-nitro-biphenyl-4-carboxylic acid | MS/APCI m/e 527 (M + 1) |
| 33 | 2'-Bromo-4'-[3-(2,6-dichloro-phenyl)-5-isopropyl-3H-[1,2,3]triazol-4-ylmethoxy]-biphenyl-4-carboxylic acid | MS/APCI m/e 560 (M + 1) |
| 34 | 4'-[3-(2-Chloro-6-fluoro-phenyl)-5-isopropyl-3H-[1,2,3]triazol-4-ylmethoxy]-2'-methyl-biphenyl-4-carboxylic acid | LC-ES/MS m/e 480.0 (M + 1) |

TABLE 2-continued

| Ex | Name | Physical Data |
|---|---|---|
| 35 | 2'-Chloro-4'-[3-(2-chloro-6-fluoro-phenyl)-5-isopropyl-3H-[1,2,3]triazol-4-ylmethoxy]-biphenyl-4-carboxylic acid | LC-ES/MS m/e 500.0 (M + 1) |
| 36 | 4'-[5-Isopropyl-3-(2-trifluoromethoxy-phenyl)-3H-[1,2,3]triazol-4-ylmethoxy]-2'-methyl-biphenyl-4-carboxylic acid | LC-ES/MS m/e 512.0 (M + 1) |
| 37 | 2'-Chloro-4'-[5-isopropyl-3-(2-trifluoromethoxy-phenyl)-3H-[1,2,3]triazol-4-ylmethoxy]-biphenyl-4-carboxylic acid | LC-ES/MS m/e 532.0 (M + 1) |
| 38 | 3-[({4-[3-(2,6-Dichloro-phenyl)-5-isopropyl-3H-[1,2,3]triazol-4-ylmethoxy]-2-methyl-phenyl}-methyl-amino)-methyl]-benzoic acid | LC-ES/MS m/e 539.2 (M + 1) |
| 39 | 3-[({4-[5-Isopropyl-3-(2-trifluoromethoxy-phenyl)-3H-[1,2,3]triazol-4-ylmethoxy]-2-methyl-phenyl}-methyl-amino)-methyl]-benzoic acid | LC-ES/MS m/e 555.0 (M + 1) |
| 40 | 3-[({4-[5-Isopropyl-3-(2-trifluoromethyl-phenyl)-3H-[1,2,3]triazol-4-ylmethoxy]-2-methyl-phenyl}-methyl-amino)-methyl]-benzoic acid | LC-ES/MS m/e 539.2 (M + 1) |
| 41 | 4-[({4-[5-Isopropyl-3-(2-trifluoromethyl-phenyl)-3H-[1,2,3]triazol-4-ylmethoxy]-2-methyl-phenyl}-methyl-amino)-methyl]-benzoic acid | LC-ES/MS m/e 539.2 (M + 1) |
| 42 | 4-[({4-[5-Isopropyl-3-(2,6-Dichloro-phenyl)-3H-[1,2,3]triazol-4-ylmethoxy]-2-methyl-phenyl}-methyl-amino)-methyl]-benzoic acid | LC-ES/MS m/e 539.0 (M + 1) |
| 43 | 6-{4-[3-(2,6-Dichloro-phenyl)-5-isopropyl-3H-[1,2,3]triazol-4-ylmethoxy]-2-methyl-phenyl}-benzo[b]thiophene-3-carboxylic acid | LC-ES/MS m/e 552.0 (M + 1) |
| 44 | 3-[({4-[3-(2-Chloro-6-fluoro-phenyl)-5-isopropyl-3H-[1,2,3]triazol-4-ylmethoxy]-2-methyl-phenyl}-methyl-amino)-methyl]-benzoic acid | LC-ES/MS m/e 523.0 (M + 1) |
| 45 | 3-{4-[3-(2,6-Dichloro-phenyl)-5-isopropyl-3H-[1,2,3]triazol-4-ylmethoxy]-2-methyl-benzylamino}-benzoic acid | LC-ES/MS m/e 523.3 (M − 1) |
| 46 | 4-[({4-[5-Cyclopropyl-3-(2,6-dichloro-phenyl)-3H-[1,2,3]triazol-4-ylmethoxy]-2-methyl-phenyl}-methyl-amino)-methyl]-2-methyl-benzoic acid | ES/MS m/e 549.0 (M − 2), 551.0 (M − 0) |
| 47 | 2-Butoxy-4-[({4-{3-(2,6-dichloro-phenyl)-5-isopropyl-3H-[1,2,3]triazol-4-ylmethoxy]-2-methyl-phenyl}-methyl-amino)-methyl]-benzoic acid | LC-ES/MS m/e 611.3 (M + 1), 609.3 (M − 1) |
| 48 | 5-{4-[3-(2,6-Dichloro-phenyl)-5-isopropyl-3H-[1,2,3]triazol-4-ylmethoxy]-phenyl}-thiophene-2-carboxylic acid | LC-ES/MS m/e 488 (M + 1), 95.8% |
| 49 | 5-{4-[5-Isopropyl-3-(2-trifluoromethoxy-phenyl)-3H-[1,2,3]triazol-4-ylmethoxy]-2-methyl-phenyl}-thiophene-2-carboxylic acid | LC-ES/MS m/e 518 (M + 1), 92.3% |
| 50 | 5-{4-[3-(2,6-Dichloro-phenyl)-5-isopropyl-3H-[1,2,3]triazol-4-ylmethoxy]-phenyl}-thiophene-2-carboxylic acid | LC-ES/MS m/e 488 (M + 1) |
| 51 | 5-{4-[5-Isopropyl-3-(2-trifluoromethoxy-phenyl)-3H-[1,2,3]triazol-4-ylmethoxy]-2-methyl-phenyl}-thiophene-2-carboxylic acid | LC-ES/MS m/e 518 (M + 1) |
| 52 | 4-[({4-[3-(2,6-Dichloro-phenyl)-5-isopropyl-3H-[1,2,3]triazol-4-ylmethoxy]-2-fluoro-phenyl}-methyl-amino)-methyl]-2-methyl-benzoic acid. | LC-ES/MS m/e 557.0 (M + 1) |
| 53 | 4'-[5-Cyclopropyl-3-(2-trifluoromethoxy-phenyl)-3H-[1,2,3]triazol-4-ylmethoxy]-2'-methyl-biphenyl-4-carboxylic acid | LC-ES/MS m/e 508.0 (M − 1) |
| 54 | 4'-[5-Cyclopropyl-3-(2,6-dichloro-phenyl)-3H-[1,2,3]triazol-4-ylmethoxy]-2'-methyl-biphenyl-4-carboxylic acid | LC-ES/MS m/e 492.0 (M − 1) |
| 55 | 4'-[3-(2,6-Dichloro-phenyl)-5-trifluoromethyl-3H-[1,2,3]triazol-4-ylmethoxy]-2'-methyl-biphenyl-4-carboxylic acid | LC-ES/MS m/e 520.0 (M − 1) |

Example 56

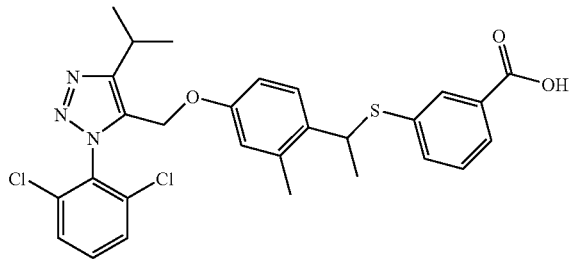

3-(1-{4-[3-(2,6-Dichloro-phenyl)-5-isopropyl-3H-[1,2,3]triazol-4-ylmethoxy]-2-methyl-phenyl}-ethylsulfanyl)-benzoic acid

Step A

To a room temperature solution of 1-{4-[3-(2,6-dichloro-phenyl)-5-isopropyl-3H-[1,2,3]triazol-4-ylmethoxy]-2-methyl-phenyl}-ethanol (70 mg, 0.167 mmol) in toluene (2 mL) are added 3-mercapto-benzoic acid methyl ester (28 mg, 0.167 mmol) and tri-N-butylphosphine (62 µL, 0.251 mmol). The reaction mixture is cooled to 0° C. To the reaction mixture is added 1,1'-(azocarbonyl)-dipiperidine (63 mg, 0.251 mmol). The reaction mixture is warmed to room temperature and stirred overnight. The reaction mixture is concentrated and the residue is chromatographed (40 g $SiO_2$, 0% to 30% EtOAc/Hexanes) to yield 3-(1-{4-[3-(2,6-Dichloro-phenyl)-5-isopropyl-3H-[1,2,3]triazol-4-ylmethoxy]-2-methyl-phenyl}-ethylsulfanyl)-benzoic acid methyl ester (62 mg, 65%).

Step B

To an ambient temperature solution of 3-(1-{4-[3-(2,6-dichloro-phenyl)-5-isopropyl-3H-[1,2,3]triazol-4-ylmethoxy]-2-methyl-phenyl}-ethylsulfanyl)-benzoic acid methyl ester (53 mg, 0.0934 mmol) in dioxane (2 mL) is added a solution of lithium hydroxide (140 µL, 0.280 mmol, 2.0N in water). The reaction is heated to 50° C. for 2 h. The reaction mixture is concentrated and the residue is diluted with $Et_2O$ and water. The aqueous layer is adjusted to pH ~4 and is extracted with a second portion of $Et_2O$. The combined organic layers are washed with water, dried ($MgSO_4$), filtered, and concentrated to yield the title compound (49 mg, 94%). LC-ES/MS m/e 556.3 (M+1), HPLC purity: 100%.

The following compounds in Table 3 are prepared essentially according to the preparation of 3-(1-{4-[3-(2,6-Dichloro-phenyl)-5-isopropyl-3H-[1,2,3]triazol-4-ylmethoxy]-2-methyl-phenyl}-ethylsulfanyl)-benzoic acid using the appropriate starting material.

TABLE 3[1]

| Ex | Name | Physical Data |
|---|---|---|
| 57 | 4-(2-{4-[3-(2,6-Dichloro-phenyl)-5-isopropyl-3H-[1,2,3]triazol-4-ylmethoxy]-phenyl}-propoxy)-benzoic acid | LC-ES/MS m/e 540.0 (M + 1), 100.0% |
| 58 | 3-(1-{4-[3-(2,6-Dichloro-phenyl)-5-isopropyl-3H-[1,2,3]triazol-4-ylmethoxy]-2-methyl-phenyl}-ethylsulfanyl)-benzoic acid | Isomer 1 LC-ES/MS m/e 556.3 (M + 1) |
| 59 | 3-(1-{4-[3-(2,6-Dichloro-phenyl)-5-isopropyl-3H-[1,2,3]triazol-4-ylmethoxy]-2-methyl-phenyl}-ethylsulfanyl)-benzoic acid | Isomer 2 LC-ES/MS m/e 556.3 (M + 1) |
| 60 | 3-(1-{4-[3-(2-Chloro-6-fluoro-phenyl)-5-isopropyl-3H-[1,2,3]triazol-4-ylmethoxy]-2-methyl-phenyl}-ethoxy)-benzoic acid | Isomer 1 LC-ES/MS m/e 523.0 (M + 1) |
| 61 | 3-(1-{4-[3-(2-Chloro-6-fluoro-phenyl)-5-isopropyl-3H-[1,2,3]triazol-4-ylmethoxy]-2-methyl-phenyl}-ethoxy)-benzoic acid | Isomer 2 LC-ES/MS m/e 523.0 (M + 1) |
| 62 | [3-(1-{4-[3-(2,6-Dichloro-phenyl)-5-isopropyl-3H-[1,2,3]triazol-4-ylmethoxy]-2-methyl-phenyl}-ethoxy)-phenyl]-acetic acid | LC-ES/MS m/e 554.0 (M + 1) |
| 63 | 3-[3-(1-{4-[3-(2,6-Dichloro-phenyl)-5-isopropyl-3H-[1,2,3]triazol-4-ylmethoxy]-2-methyl-phenyl}-ethoxy)-phenyl]-propionic acid | LC-ES/MS m/e 568.0 (M + 1) |
| 64 | 3-[({4-[3-(2,6-Dichloro-phenyl)-5-trifluoromethyl-3H-[1,2,3]triazol-4-ylmethoxy]-2-methyl-phenyl}-methyl-amino)methyl]-benzoic acid | LC-ES/MS m/e 563.0 (M − 1) |
| 65 | 3[({4-[5-Cyclopropyl-3-(2-trifluoromethoxy-phenyl)-3H-[1,2,3]triazol-4-ylmethoxy]-2-methyl-phenyl}-methyl-amino)-methyl]-benzoic acid | LC-ES/MS m/e 551.0 (M − 1) |
| 66 | 4-[({4-[3-(2,6-Dichloro-phenyl)-5-trifluoromethyl-3H-[1,2,3]triazol-4-ylmethoxy]-2-methyl-phenyl}-methyl-amino)-methyl]-2-trifluoromethyl-benzoic acid | LC-ES/MS m/e 631.0 (M − 1) |
| 67 | 4-[({4-[5-Cyclopropyl-3-(2-trifluoromethoxy-phenyl)-3H-[1,2,3]triazol-4-ylmethoxy]-2-methyl-phenyl}-methyl-amino)-methyl]-2-trifluoromethyl-benzoic acid | LC-ES/MS m/e 619.0 (M − 1) |
| 68 | 4-[({4-[5-Isopropyl-3-(2-trifluoromethoxy-phenyl)-3H-[1,2,3]triazol-4-ylmethoxy]-2-methyl-phenyl}-methyl-amino)-methyl]-2-trifluoromethyl-benzoic acid | LC-ES/MS m/e 621.0 (M − 1) |
| 69 | 4-[({4-[5-Cyclopropyl-3-(2,6-dichloro-phenyl)-3H-[1,2,3]triazol-4-ylmethoxy]-2-methyl-phenyl}-methyl-amino)-methyl]-2-trifluoromethyl-benzoic acid | LC-ES/MS m/e 603.0 (M − 1) |
| 70 | 4-[({4-[3-(2,6-Dichloro-phenyl)-5-isopropyl-3H-[1,2,3]triazol-4-ylmethoxy]-2-methyl-phenyl}-methyl-amino)-methyl]-2-trifluoromethyl-benzoic acid | LC-ES/MS m/e 605.0 (M − 1) |

TABLE 3[1]-continued

| Ex | Name | Physical Data |
|---|---|---|
| 71 | 6-{4-[3-(2,6-Dichloro-phenyl)-5-trifluoromethyl-3H-[1,2,3]triazol-4-ylmethoxy]-2-methyl-phenyl}-benzo[d]isothiazole-3-carboxylic acid | LC-ES/MS m/e 577.0 (M − 1) |
| 72 | 4-[({4-[5-Cyclopropyl-3-(2-trifluoromethoxy-phenyl)-3H-[1,2,3]triazol-4-ylmethoxy]-2-methyl-phenyl}-methyl-amino)-methyl]-2-methyl-benzoic acid | LC-ES/MS m/e 565.0 (M − 1) |

[1]When present, individual enantiomers are isolated from the racemic mixture via chiral chromatography. Isomer 1 elutes from the column first and isomer 2 elutes from the column second.

Example 73

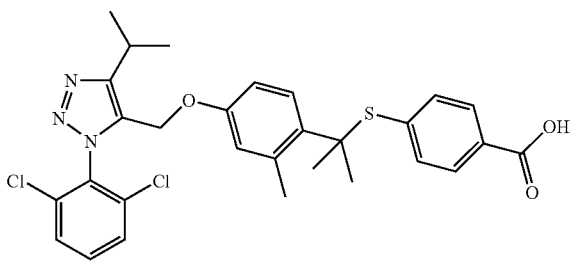

4-(1-{4-[3-(2,6-Dichloro-phenyl)-5-isopropyl-3H-[1,2,3]triazol-4-ylmethoxy]-2-methyl-phenyl}-1-methyl-ethylsulfanyl)-benzoic acid

Step A

To an ambient temperature solution of 2-{4-[3-(2,6-dichloro-phenyl)-5-isopropyl-3H-[1,2,3]triazol-4-yl-methoxy]-2-methyl-phenyl}-propan-2-ol (100 mg, 0.230 mmol) in DCE (1 mL) is added zinc iodide (37 mg, 0.115 mmol). The reaction is stirred at room temperature for 10 min. A solution of methyl 4-mercaptobenzoate (38 mg, 0.225 mmol) in DCE (1 mL) is added and the reaction is stirred overnight at room temperature. The reaction is concentrated under reduced pressure and the residue is chromatographed ($SiO_2$ 40 g, 0% to 30% EtOAC/Hexane to yield 4-(1-{4-[3-(2,6-dichloro-phenyl)-5-isopropyl-3H-[1,2,3]triazol-4-yl-methoxy]-2-methyl-phenyl}-1-methyl-ethylsulfanyl)-benzoic acid methyl ester (114 mg, 87%). $^1$H NMR (400 MHz, $CDCl_3$) δ 7.81 (d, 2H, J=7.9 Hz), 7.52-7.39 (m, 3H), 7.22 (s, 1H), 7.16 (d, 2H, J=7.8 Hz), 7.11 (d, 1H, J=8.4 Hz), 6.63 (d, 1H, J=8.4 Hz), 4.90 (s, 2H), 3.90 (s, 3H), 3.23 (sept, 1H, J=6.6 Hz), 2.01 (s, 3H), 1.64 (s, 6H), 1.46 (d, 6H, J=6.6 Hz).

Step B

To an ambient temperature solution of 3-(1-{4-[3-(2,6-Dichloro-phenyl)-5-isopropyl-3H-[1,2,3]triazol-4-yl-methoxy]-2-methyl-phenyl}-1-methyl-ethylsulfanyl)-benzoic acid methyl ester (110 mg, 0.188 mmol) in dioxane (2 mL) is added a solution of lithium hydroxide (282 µL, 0.564 mmol, 2.0N in water). The reaction is heated to 50° C. for 2 h. The reaction is concentrated and the residue is diluted with $Et_2O$ and water. The aqueous layer is adjusted to pH ~4 and extracted with a second portion of $Et_2O$. The combined organic layers are washed with water, dried ($MgSO_4$), filtered, and concentrated to yield the title compound (106 mg, 99%). LC/MS (ES+): 570.0, 100.0%.

The following compounds in Table 4 are prepared essentially according to the preparation of 4-(1-{4-[3-(2,6-Dichloro-phenyl)-5-isopropyl-3H-[1,2,3]triazol-4-yl-methoxy]-2-methyl-phenyl}-1-methyl-ethylsulfanyl)-benzoic acid using the appropriate starting material.

TABLE 4

| Ex | Name | Physical Data |
|---|---|---|
| 74 | 3-(1-{4-[3-(2,6-Dichloro-phenyl)-5-isopropyl-3H-[1,2,3]triazol-4-ylmethoxy]-phenyl}-1-methyl-ethylsulfanyl)-benzoic acid | LC/MS (ES+): 556.0, |
| 75 | 4-(1-{4-[3-(2,6-Dichloro-phenyl)-5-isopropyl-3H-[1,2,3]triazol-4-ylmethoxy]-phenyl}-1-methyl-ethylsulfanyl)-benzoic acid | LC/MS (ES+): 556.0, |
| 76 | [3-(1-{4-[3-(2,6-Dichloro-phenyl)-5-isopropyl-3H-[1,2,3]triazol-4-ylmethoxy]-phenyl}-1-methyl-ethylsulfanyl)-phenyl]-acetic acid | LC/MS (ES+): 570.0, |
| 77 | [4-(1-{4-[3-(2,6-Dichloro-phenyl)-5-isopropyl-3H-[1,2,3]triazol-4-ylmethoxy]-phenyl}-1-methyl-ethylsulfanyl)-phenyl]-acetic acid | LC/MS (ES+): 570.0, |
| 78 | 3-(1-{4-[3-(2,6-Dichloro-phenyl)-5-isopropyl-3H-[1,2,3]triazol-4-ylmethoxy]-2-methyl-phenyl}-1-methyl-ethylsulfanyl)-benzoic acid | LC/MS (ES+): 570.0 |
| 79 | 4-(1-{4-[3-(2,6-Dichloro-phenyl)-5-isopropyl-3H-[1,2,3]triazol-4-ylmethoxy]-2-methyl-phenyl}-1-methyl-ethylsulfanyl)-benzoic acid | LC/MS (ES+): 570.0, |
| 80 | [3-(1-{4-[3-(2,6-Dichloro-phenyl)-5-isopropyl-3H-[1,2,3]triazol-4-ylmethoxy]-2-methyl-phenyl}-1-methyl-ethylsulfanyl)-phenyl]-acetic acid | LC/MS (ES+): 584.0, |
| 81 | [4-(1-{4-[3-(2,6-Dichloro-phenyl)-5-isopropyl-3H-[1,2,3]triazol-4-ylmethoxy]-2-methyl-phenyl}-1-methyl-ethylsulfanyl)-phenyl]-acetic acid | LC/MS (ES+): 584.0, |
| 82 | 3-(1-{4-[3-(2,6-Dichloro-phenyl)-5-isopropyl-3H-[1,2,3]triazol-4-ylmethoxy]-3-methyl-phenyl}-1-methyl-ethylsulfanyl)-benzoic acid | LC/MS (ES+): 570.0, |
| 83 | 4-(1-{4-[3-(2,6-Dichloro-phenyl)-5-isopropyl-3H-[1,2,3]triazol-4-ylmethoxy]-3-methyl-phenyl}-1-methyl-ethylsulfanyl)-benzoic acid | LC/MS (ES+): 570.0, |
| 84 | [3-(1-{4-[3-(2,6-Dichloro-phenyl)-5-isopropyl-3H-[1,2,3]triazol-4-ylmethoxy]-3-methyl-phenyl}-1-methyl-ethylsulfanyl)-phenyl]-acetic acid | LC/MS (ES+): 584.0, |
| 85 | [4-(1-{4-[3-(2,6-Dichloro-phenyl)-5-isopropyl-3H-[1,2,3]triazol-4-ylmethoxy]-3-methyl-phenyl}-1-methyl-ethylsulfanyl)-phenyl]-acetic acid | LC/MS (ES+): 584.0, |

Example 86

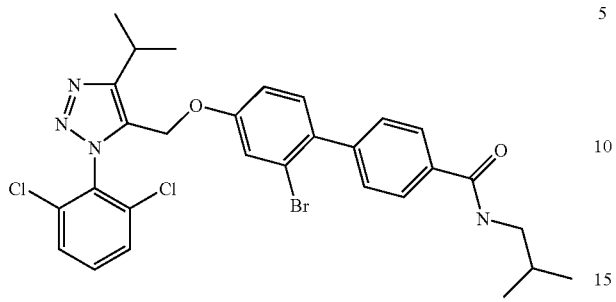

2'-Bromo-4'-[3-(2,6-dichloro-phenyl)-5-isopropyl-3H-[1,2,3]triazol-4-ylmethoxy]-biphenyl-4-carboxylic acid isobutyl-amide

Step A

To thionyl chloride (1.5 mL, 20 mmol) is added 2'-bromo-4'-[3-(2,6-dichloro-phenyl)-5-isopropyl-3H-[1,2,3]triazol-4-ylmethoxy]-biphenyl-4-carboxylic acid (0.074 g, 0.13 mmol). The reaction is stirred overnight at room temperature. The reaction mixture is concentrated under reduced pressure to give 2'-Bromo-4'-[3-(2,6-dichloro-phenyl)-5-isopropyl-3H-[1,2,3]triazol-4-ylmethoxy]-biphenyl-4-carbonyl chloride.

Step B

To 2'-bromo-4'-[3-(2,6-dichloro-phenyl)-5-isopropyl-3H-[1,2,3]triazol-4-ylmethoxy]-biphenyl-4-carbonyl chloride (0.043 mmol) in dichloromethane (2 mL) is added s-butyl amine (0.05 mL, 0.5 mmol). The reaction is stirred at room temperature for 1 h and concentrated under reduced pressure. The residue is slurried in 1 N hydrochloric acid, and the solid is filtered to give the title compound (0.011 g). ES/MS m/e 617.0 (M+1).

The following compounds in Table 5 are prepared essentially according to the preparation of 2'-Bromo-4'-[3-(2,6-dichloro-phenyl)-5-isopropyl-3H-[1,2,3]triazol-4-ylmethoxy]-biphenyl-4-carboxylic acid isobutyl-amide using the appropriate starting material.

TABLE 5

| Ex | Chemical Name | Physical Data |
|---|---|---|
| 87 | 2'-Bromo-4'-[3-(2,6-dichloro-phenyl)-5-isopropyl-3H-[1,2,3]triazol-4-ylmethoxy]-biphenyl-4-carboxylic acid ethylamide | MS/ES m/e 589.0 (M + 1) |
| 88 | 2'-Bromo-4'-[3-(2,6-dichloro-phenyl)-5-isopropyl-3H-[1,2,3]triazol-4-ylmethoxy]-biphenyl-4-carboxylic acid methylamide | MS/ES m/e 574.8 (M + 1) |
| 89 | 4'-[3-(2,6-Dichloro-phenyl)-5-isopropyl-3H-[1,2,3]triazol-4-ylmethoxy]-2'-methyl-biphenyl-4-carboxylic acid ethylamide | ES/MS m/e ($^{35}$Cl) 523.0 (M + 1) |

Example 90

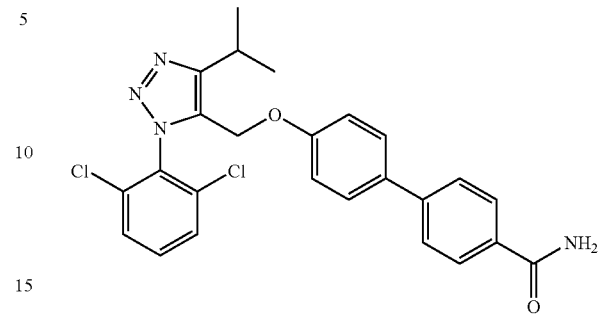

4'-[3-(2,6-Dichloro-phenyl)-5-isopropyl-3H-[1,2,3]triazol-4-ylmethoxy]-biphenyl-4-carboxylic acid amide To a solution of 4'-[3-(2,6-dichloro-phenyl)-5-isopropyl-3H-[1,2,3]triazol-4-ylmethoxy]-biphenyl-4-carbonitrile (0.150 mg) in dimethyl sulfoxide (1.2 mL) is added potassium carbonate (0.03 g) and 50% aqueous hydrogen peroxide (0.2 mL). The reaction mixture is allowed to stir at room temperature for 30 minutes. The reaction mixture is diluted with water (55 mL), cooled to 0° C., and filtered. The resulting solids are washed with cold (−78° C.) hexanes. The white solids are allowed to dry under reduced pressure to give the title compound (0.100 g, 64%). $^1$H NMR (300 MHz, CDCl$_3$) δ 7.9 (d, 2H), 7.6 (d, 2H), 7.5 (m, 5H), 6.9 (d, 2H), 5.0 (s, 2H), 3.3 (p, 1H), 1.5 (d, 6H);' APCI/MS m/e 481 (M+1), HPLC purity 98.5%.

Example 91

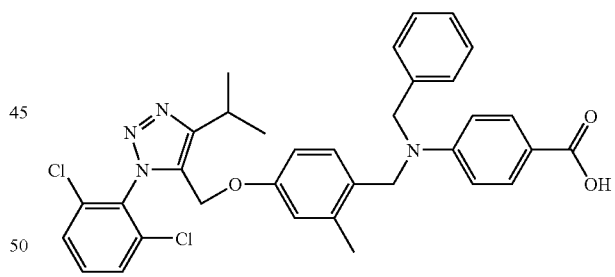

4-(Benzyl-{4-[3-(2,6-dichloro-phenyl)-5-isopropyl-3H-[1,2,3]triazol-4-ylmethoxy]-2-methyl-benzyl}-amino)-benzoic acid

Step A

To a 0° C. solution of [3-(2,6-dichloro-phenyl)-5-isopropyl-3H-[1,2,3]triazol-4-yl]-methanol (309 mg, 1.08 mmol), 4-(4-hydroxy-2-methyl-benzylamino)-benzoic acid methyl ester (292 mg, 1.08 mmol), and tri-n-butylphosphine (344 mg, 1.70 mmol) in toluene (50 mL) is added 1,1'-(Azodicarbonyl)-dipiperidine (450 mg, 1.78 mmol). The reaction mixture is stirred for 1.5 h. The reaction mixture is diluted with heptane, filtered, and concentrated under reduced pressure.

The residue is purified by flash chromatography (40 g silica, gradient EtOAc/Hexane) to give 4-{4-[3-(2,6-Dichloro-phenyl)-5-isopropyl-3H-[1,2,3]triazol-4-ylmethoxy]-2-methyl-benzylamino}-benzoic acid methyl ester (309 mg, 1.08 mmol). MS: 539.0 (M+1).

Step B

A solution of 4-{4-[3-(2,6-dichloro-phenyl)-5-isopropyl-3H-[1,2,3]triazol-4-ylmethoxy]-2-methyl-benzylamino}-benzoic acid methyl ester (90 mg, 0.17 mmol) and benzaldehyde (28 mg, 0.26 mmol) is stirred at room temperature for 30 minutes. Sodium triacetoxy borohydride (265 mg, 1.25 mmol) is added to the reaction mixture and stirred over night. The reaction mixture is concentrated under reduced pressure and partitioned between ethyl acetate and saturated sodium bicarbonate. The layers are separated and the aqueous layer is extracted with ethyl acetate (2×). The combined ethyl acetate layers are dried (MgSO₄) and concentrated under reduced pressure. The residue is purified by flash chromatography on 12 g silica with ethyl acetate in heptane gradient to provide 4-{4-[3-(2,6-Dichloro-phenyl)-5-isopropyl-3H-[1,2,3]triazol-4-ylmethoxy]-2-methyl-benzylamino}-benzoic acid methyl ester (32 mg, 30%). MS: 629.0 (M+1). LC-MS: 613.3 (M−1).

Example 92

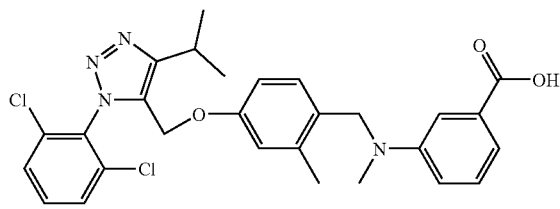

3-({4-[3-(2,6-Dichloro-phenyl)-5-isopropyl-3H-[1,2,3]triazol-4-ylmethoxy]-2-methyl-benzyl}-methyl-amino)-benzoic acid Step A To a mixture of 3-{4-[3-(2,6-dichloro-phenyl)-5-isopropyl-3H-[1,2,3]triazol-4-ylmethoxy]-2-methyl-benzylamino}-benzoic acid ethyl ester (160 mg, 0.29 mmol) and sodium hydride (13 mg, 0.33 mmol) in anhydrous N,N-dimethyl formamide is added iodomethane (50 mg, 0.35 mmol). After three hours, more iodomethane (50 mg, 0.35 mmol) is added and the mixture is heated to 60° C. After three hours, more iodomethane (50 mg, 0.35 mmol) is added and the mixture is stirred at room temperature overnight. The mixture is then partitioned between diethylether and water. The aqueous layer is extracted three times with diethylether. The combined ether layers are dried (MgSO4) and concentrated under reduced pressure. The crude residue is purified on 12 g of silica with ethyl acetate in heptane gradient to provide 3-({4-[3-(2,6-Dichloro-phenyl)-5-isopropyl-3H-[1,2,3]triazol-4-ylmethoxy]-2-methyl-benzyl}-methyl-amino)-benzoic acid ethyl ester (20 mg, 12%) LC-MS: 567.0 (M+1).

Step B

To a solution of 3-({4-[3-(2,6-Dichloro-phenyl)-5-isopropyl-3H-[1,2,3]triazol-4-ylmethoxy]-2-methyl-benzyl}-methyl-amino)-benzoic acid ethyl ester (20 mg, 0.035 mmol) in THF (4.0 mL) and methanol (4.0 mL) is added 5 M NaOH (0.5 mL). The reaction mixture is heated to 70° C. for two hours and cooled to room temperature. A solution of 5 M HCl (0.5 mL) is added. The reaction mixture is concentrated and triturated with methanol and then water is added to precipitate the product. The title compound (10 mg, 53%) is collected by vacuum filtration as a white solid. LC-MS: 537.3 (M−1).

Example 93

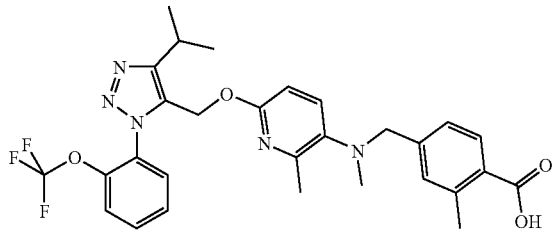

4-[({6-[5-Isopropyl-3-(2-trifluoromethoxy-phenyl)-3H-[1,2,3]triazol-4-ylmethoxy]-2-methyl-pyridin-3-yl}-methyl-amino)-methyl]-2-methyl-benzoic acid Step A To an ambient temperature solution of [5-isopropyl-3-(2-trifluoromethoxy-phenyl)-3H-[1,2,3]triazol-4-yl]-methanol (2.0 g, 6.64 mmol) in degassed toluene (22 mL) are added 6-chloro-2-methyl-3-nitro-pyridine (1.15 g, 6.64 mmol), cesium carbonate (3.25 g, 9.96 mmol), 2-(di-t-butylphosphino)-1,1'-binapthyl (332 mg, 0.833 mmol, 12.5 mol %), and palladium (II) acetate (150 mg, 0.666 mmol, 10 mol %). The reaction mixture is heated to 70° C. overnight. The reaction is filtered through a pad of diatomaceous earth. The filtrate is concentrated and the residue is chromatographed (SiO₂ 120 g, 0% to 20% EtOAc/Hexane to yield 6-[5-Isopropyl-3-(2-trifluoromethoxy-phenyl)-3H-[1,2,3]triazol-4-ylmethoxy]-2-methyl-3-nitro-pyridine (2.78 g, 96%). ¹H NMR (400 MHz, CDCl₃) δ 8.23 (d, 1H, J=8.8 Hz), 7.61-7.53 (m, 2H), 7.48-7.42 (m, 2H), 6.51 (d, 1H, J=8.8 Hz), 5.42 (s, 2H), 3.26 (sept, 1H, J=7.0 Hz), 2.71 (s, 3H), 1.43 (d, 6H, J=7.0 Hz).

Step B

To a room temperature solution of 6-[5-isopropyl-3-(2-trifluoromethoxy-phenyl)-3H-[1,2,3]triazol-4-ylmethoxy]-2-methyl-3-nitro-pyridine (2.78 g, 6.35 mmol) in EtOH/THF (1/1, 200 mL) is added platinum (II) oxide (144 mg, 0.636 mmol, 10 mol %). The mixture is stirred under an atmosphere of hydrogen gas. After 3 h, the reaction is filtered through diatomaceous earth. The filtrate is concentrated and the residue is chromatographed (SiO₂ 120 g, 0% to 30% EtOAc/Hexane to yield 6-[5-isopropyl-3-(2-trifluoromethoxy-phenyl)-3H-[1,2,3]triazol-4-ylmethoxy]-2-methyl-pyridin-3-ylamine (2.28 g, 88%). ¹H NMR (400 MHz, CDCl₃) δ 7.57-7.51 (m, 2H), 7.46-7.38 (m, 2H), 6.92 (d, 1H, J=8.4 Hz), 6.26 (d, 1H, J=8.4 Hz), 5.25 (s, 2H), 3.29 (sept, 1H, J=7.0 Hz), 2.24 (s, 3H), 1.40 (d, 6H, J=7.0 Hz).

Step C

To a room temperature solution of 6-[5-isopropyl-3-(2-trifluoromethoxy-phenyl)-3H-[1,2,3]triazol-4-ylmethoxy]-

2-methyl-pyridin-3-ylamine (150 mg, 0.369 mmol) in MeOH (6 mL) is added 4-formyl-2-methyl-benzoic acid methyl ester (72 mg, 0.406 mmol), and the mixture is stirred for 10 min. Decaborane (14 mg, 0.0738 mmol) is added. After 2 h, formaldehyde (2.0 mL, 37 wt % in water) is added and the reaction is stirred for 10 minutes. A second portion of decaborane (14 mg, 0.0738 mmol) is added. After 2 h, the reaction is concentrated and the residue is chromatographed (SiO$_2$ 40 g, 0% to 20% EtOAc/Hexane to yield 4-[({6-[5-Isopropyl-3-(2-trifluoromethoxy-phenyl)-3H-[1,2,3]triazol-4-ylmethoxy]-2-methyl-pyridin-3-yl}-methyl-amino)-methyl]-2-methyl-benzoic acid methyl ester (156 mg, 73%). $^1$H NMR (400 MHz, DMSO) δ 7.77-7.72 (m, 1H), 7.70 (d, 2H, J=7.9 Hz), 7.66-7.61 (m, 1H), 7.59-7.53 (m, 1H), 7.46 (d, 1H, J=8.8 Hz), 7.23-7.19 (m, 2H), 6.37 (d, 1H, J=8.4 Hz), 5.27 (s, 2H), 3.95 (s, 2H), 3.79 (s, 3H), 3.28 (sept, 1H, J=6.6 Hz), 2.47 (s, 6H), 2.32 (s, 3H), 1.28 (d, 6H, J=6.6 Hz).

Step D

A solution of 4-[({6-[5-isopropyl-3-(2-trifluoromethoxy-phenyl)-3H-[1,2,3]triazol-4-ylmethoxy]-2-methyl-pyridin-3-yl}-methyl-amino)-methyl]-2-methyl-benzoic acid methyl ester (147 mg, 0.251 mmol) in dioxane (2 mL) is treated with a solution of lithium hydroxide (378 mL, 0.756 mmol, 2.0N in water) and heated to 50° C. After 2 h, the reaction is concentrated and the residue is partitioned between Et$_2$O and water. The aqueous layer is adjusted to pH ~7 and is extracted with a second portion of Et$_2$O. The combined organic layers are washed with water, dried (MgSO$_4$), filtered, and concentrated to yield the title compound (138 mg, 97%). LC/MS (ES+): 570.0, 100%.

Example 94

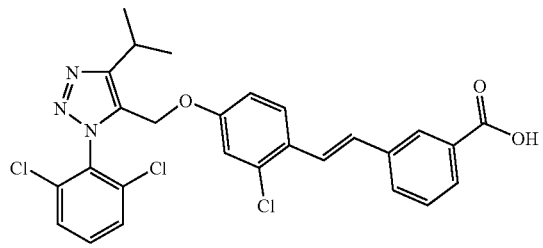

3-(2-{2-Chloro-4-[3-(2,6-dichloro-phenyl)-5-isopropyl-3H-[1,2,3]triazol-4-ylmethoxy]-phenyl}-vinyl)-benzoic acid Step A To solution of [3-(2,6-dichloro-phenyl)-5-isopropyl-3H-[1,2,3]triazol-4-yl]-methanol (0.100 g, 1 eq) and 2-chloro-4-fluorobenzaldehyde (0.11 g, 2 eq) in dimethylformamide (3 mL) is added cesium carbonate (0.23 g, 2 eq). The reaction is heated to 100° C. overnight. The reaction is cooled to room temperature and water is added. The mixture is extracted with ethyl acetate and the organic layers are washed with brine, dried over sodium sulfate, filtered, and concentrated under reduced pressure. The residue is purified via flash chromatography eluting with 0-10% ethyl acetate:toluene to give 0.101 g of 2-Chloro-4-[3-(2,6-dichloro-phenyl)-5-isopropyl-3H-[1,2,3]triazol-4-ylmethoxy]-benzaldehyde. ES/MS m/e 426.1 (M+1).

Step B

To triethyl phosphate (0.75 mL, 1 eq) is added methyl 4-(bromomethyl)benzoate (1.0 g, 1 eq). The reaction is heated to 100° C. overnight. The reaction mixture is purified via flash chromatography eluting with a step gradient of 0% to 5% to 10% methyl alcohol:chloroform to give 3-(Diethoxy-pThosphorylmethyl)-benzoic acid methyl ester (0.763 g).

Step C

To a 0° C. solution of 3-(diethoxy-phosphorylmethyl)-benzoic acid methyl ester (1.2 g, 4 eq) in diethyl ether (15 mL) is added sodium hydride (0.17 g, 4 eq). After 1 h, 2-chloro-4-[3-(2,6-dichloro-phenyl)-5-isopropyl-3H-[1,2,3]triazol-4-ylmethoxy]-benzaldehyde (0.44 g, 1 eq) in diethyl ether (5 mL) is added and the reaction is stirred overnight. Upon completion, the reaction is quenched with water. The aqueous solution is acidified with 1N HCl and extracted two times with ethyl acetate. The organic layers are combined, washed with brine, dried over sodium sulfate, filtered, and concentrated under reduced pressure. The residue is purified via filter chromatography eluting with 10% ethyl acetate:toluene to give 3-(2-{2-Chloro-4-[3-(2,6-dichloro-phenyl)-5-isopropyl-3H-[1,2,3]triazol-4-ylmethoxy]-phenyl}-vinyl)-benzoic acid methyl ester (0.459 g).

Step D

To a solution of 3-(2-{2-chloro-4-[3-(2,6-dichloro-phenyl)-5-isopropyl-3H-[1,2,3]triazol-4-ylmethoxy]-phenyl}-vinyl)-benzoic acid methyl ester (0.459 g, 0.825 mmol) in methyl alcohol (20 mL) is added 1 N sodium hydroxide solution (2.5 mL). The reaction is heated to mild reflux for 1 h and is cooled to room temperature. The reaction mixture is concentrated under reduced pressure. The residue is dissolved in water and the aqueous solution is acidified with 5 N hydrochloric acid solution to form a white precipitate. The solid is filtered and dried overnight under reduced pressure to give the title compound (0.395 g). ES/MS m/e 542.0 (M+1), 542.0 (M-H); HPLC purity: 95.56

Example 95

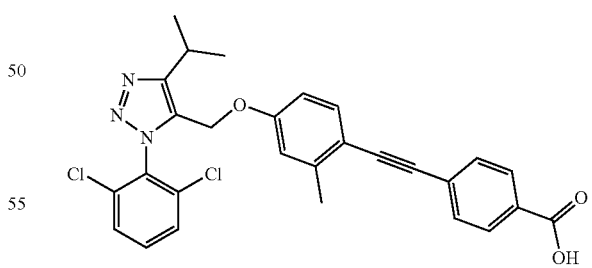

4-{4-[3-(2,6-Dichloro-phenyl)-5-isopropyl-3H-[1,2,3]triazol-4-ylmethoxy-]-2-methyl-phenylethynyl}-benzoic acid Step A To a room temperature solution of 5-(4-bromo-3-methyl-phenoxymethyl)-1-(2,6-dichloro-phenyl)-4-isopropyl-1H-

[1,2,3]triazole (50 mg, 0.110 mmol) in DMF (1 mL) are added 4-ethynyl-benzoic acid methyl ester (18 mg, 0.110 mmol) and triethylamine (107 μL, 0.770 mmol). The reaction mixture is degassed for 20 minutes with nitrogen. To the reaction mixture are added dichloro(bistriphenylphosphine) palladium (II) (8 mg, 0.011 mmol, 10 mol %) and zinc (II) triflate (40 mg, 0.110 mmol). The reaction mixture is heated to 80° C. After 3 h, the reaction is concentrated and the residue is chromatographed (40 g SiO$_2$, 0% to 5% EtOAc/Hexanes) to yield 4-{4-[3-(2,6-Dichloro-phenyl)-5-isopropyl-3H-[1,2,3]triazol-4-ylmethoxy]-2-methyl-phenylethynyl}-benzoic acid methyl ester (38 mg, 64%). LC/MS m/e 534.2 (M+1).

Step B

To an ambient temperature solution of 4-{4-[3-(2,6-Dichloro-phenyl)-5-isopropyl-3H-[1,2,3]triazol-4-ylmethoxy]-2-methyl-phenylethynyl}-benzoic acid methyl ester (32 mg, 0.0599 mmol) in dioxane (2 mL) is added a solution of lithium hydroxide (90 μL, 0.180 mmol, 2.0N in water). The reaction mixture is stirred at room temperature overnight. The reaction is concentrated and the residue is partitioned between Et$_2$O and water. The aqueous layer pH is adjusted to approximately 4 and the aqueous layer is extracted with a second portion of Et$_2$O. The combined organic layers are washed with water, dried (MgSO$_4$), filtered, and concentrated to yield the title compound (32 mg, quant). LC-ES/MS m/e 520.2 (M+1), HPLC purity: 100%.

Example 96

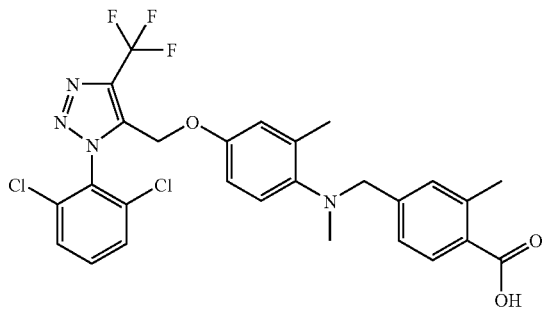

4-[({4-[3-(2,6-dichlorophenyl)-5-trifluoromethyl-3H-[1,2,3]triazol-4-ylmethoxy]-2-methylphenyl}-methylamino)-methyl]-2-methyl-benzoic acid Step A To a solution of 5-bromomethyl-1-(2,6-dichlorophenyl)-4-trifluoromethyl-1H-triazole (15.65 g, 41.7 mmol) and 4-{[(4-hydroxy-2-methylphenyl)methylamino]methyl}-2-methyl benzoic acid, methyl ester (12.49 g, 41.7 mmol) in acetonitrile (120 mL) is added potassium carbonate (11.54 g, 83.4 mmol) at room temperature. The mixture is heated at 90° C. overnight. After 16 h, the reaction is cooled to room temperature and filtered through a pad of diatomaceous earth. The solvent is removed under reduced pressure. The residue is diluted with MTBE and washed with 2N NaOH, water, and brine. The organic layer is dried over magnesium sulfate, filtered, and evaporated to afford 4-[({4-[3-(2,6-dichlorophenyl)-5-trifluoromethyl-3H-[1,2,3]triazol-4-ylmethoxy]-2-methylphenyl}-methylamino)-methyl]-2-methyl-benzoic acid methyl ester (24.2 g, 97%). ES/MS m/e 593 (M+1).

Step B

To a solution of 4-[({4-[3-(2,6-dichlorophenyl)-5-trifluoromethyl-3H-[1,2,3]triazol-4-ylmethoxy]-2-methylphenyl}-methylamino)-methyl]-2-methyl-benzoic acid methyl ester (24.2 g, 40.7 mmol) in MeOH (150 mL) and THF (150 mL) is added 2N potassium hydroxide (102 mL, 203 mmol). The mixture is heated at 60° C. for 2 hours. The solvent is removed under reduced pressure. The residue is diluted with water, acidified to pH 3 with 2N HCl, and extracted with dichloromethane. The organic layer is dried over magnesium sulfate, filtered, and evaporated under reduced pressure to afford the title compound as a white solid that is crystallized from MeOH (20 g, 80%). ES/MS m/e 579 (M+1).

Example 97

6-{4-[3-(2,6-Dichloro-phenyl)-5-trifluoromethyl-3H-[1,2,3]triazol-4-ylmethoxy]-2-methyl-phenyl}-benzo[b]thiophene-3-carboxylic acid

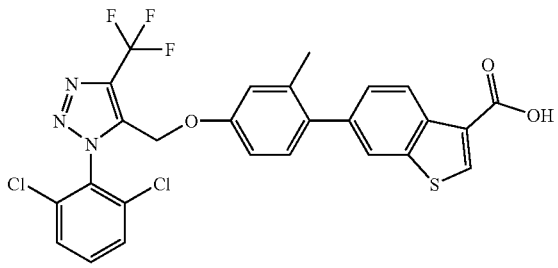

Step 1

6-{4-[3-(2,6-Dichloro-phenyl)-5-trifluoromethyl-3H-[1,2,3]triazol-4-ylmethoxy]-2-methyl-phenyl}-benzo[b]thiophene-3-carboxylic acid methyl ester

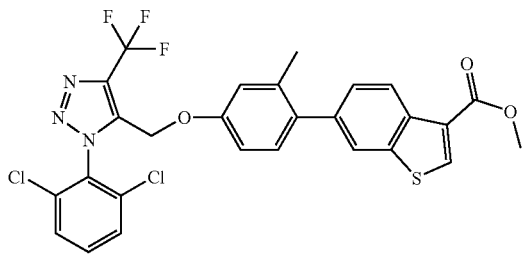

Nitrogen is bubbled through a solution of [3-(2,6-dichlorophenyl)-5-isopropyl-3H-[1,2,3]triazol-4-yl]-methanol (0.2 g, 0.64 mmol) and 6-(4-hydroxy-2-methyl-phenyl)-benzo[b]thiophene-3-carboxylic acid methyl ester (0.16 g, 0.53 mmol) in toluene (5 mL) for 10 minutes. Tri-n-butyl phosphine (0.2 mL, 0.81 mmol) is added. Nitrogen is bubbled for an additional 10 minutes followed by addition of 1,1'-(azocarbonyl)-dipiperidine (202 mg, 0.801 mmol). The reaction is stirred at room temperature for 18 h. The crude reaction is concentrated onto silica and chromatographed (40 g SiO$_2$, 0% to 30% EtOAc/Hexanes) to yield the title compound (0.140 g, 44%). ES/MS m/e 592.0 (M+1).

Step 2

6-{4-[3-(2,6-Dichloro-phenyl)-5-trifluoromethyl-3H-[1,2,3]triazol-4-ylmethoxy]-2-methyl-phenyl}-benzo[b]thiophene-3-carboxylic acid

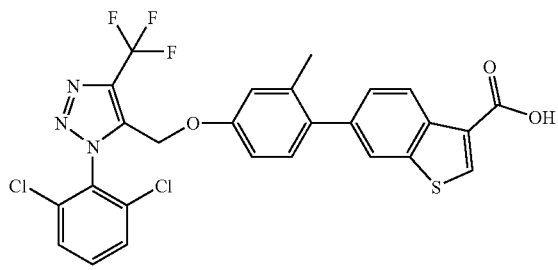

To a solution of 6-{4-[3-(2,6-Dichloro-phenyl)-5-trifluoromethyl-3H-[1,2,3]triazol-4-ylmethoxy]-2-methyl-phenyl}-benzo[b]thiophene-3-carboxylic acid methyl ester (0.14 g, 0.23 mmol) in a 1:1:1 mixture of THF, methanol, water (3 mL) is added LiOH (0.10 g, 2.36 mmol). The reaction is stirred for 18 h at room temperature. The reaction is adjusted to pH 3 with 1N HCl and extracted with EtOAc to yield the title compound (0.09 g, 66%). LC-ES/MS m/e 576.0 (M−1).

Example 98

6-{4-[3-(2,6-Dichloro-phenyl)-5-trifluoromethyl-3H-[1,2,3]triazol-4-ylmethoxy]-2-methyl-phenyl}-1-isopropyl-1H-indazole-3-carboxylic acid

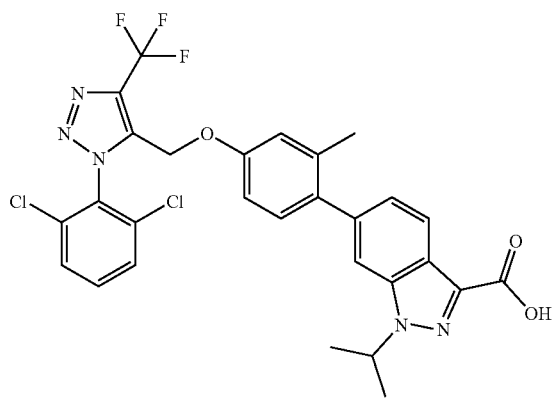

Step 1

6-{4-[3-(2,6-Dichloro-phenyl)-5-trifluoromethyl-3H-[1,2,3]triazol-4-ylmethoxy-]-2-methyl-phenyl}-1-isopropyl-1H-indazole-3-carboxylic acid methyl ester

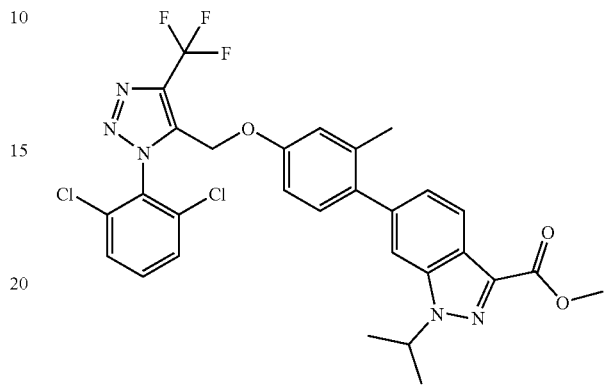

Nitrogen is bubbled through a solution of [3-(2,6-dichloro-phenyl)-5-isopropyl-3H-[1,2,3]triazol-4-yl]-methanol (0.25 g, 0.80 mmol) and 6-(4-hydroxy-2-methyl-phenyl)-1-isopropyl-1H-indazole-3-carboxylic acid methyl ester (0.2 g, 0.62 mmol) in toluene (10 mL) for 10 minutes. Tri-n-butyl phosphine (0.21 mL, 1.05 mmol) is added. Nitrogen is bubbled for an additional 10 minutes followed by addition of 1,1'-(azo-carbonyl)-dipiperidine (0.27 g, 1.05 mmol). The reaction is stirred at room temperature for 18 hours. The crude reaction is concentrated onto silica and chromatographed (40 g SiO$_2$, 0% to 50% EtOAc/Hexanes) to yield the title compound (0.28 g, 73%). LC-ES/MS m/e 618.0 (M+1).

Step 2

6-{4-[3-(2,6-Dichloro-phenyl)-5-trifluoromethyl-3H-[1,2,3]triazol-4-ylmethoxy]-2-methyl-phenyl}-1-isopropyl-1H-indazole-3-carboxylic acid

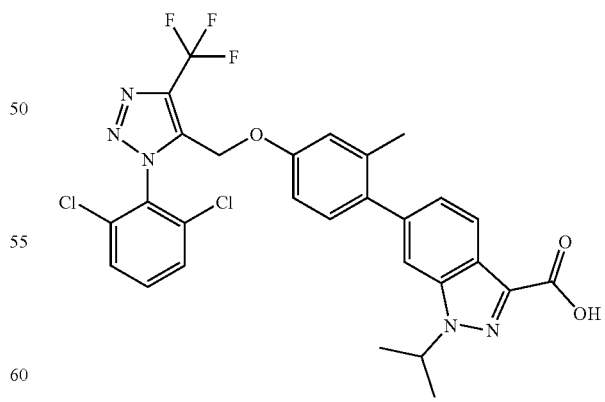

To a solution of 6-{4-[3-(2,6-dichloro-phenyl)-5-trifluoromethyl-3H-[1,2,3]triazol-4-ylmethoxy]-2-methyl-phenyl}-1-isopropyl-1H-indazole-3-carboxylic acid methyl ester (0.13 g, 0.21 mmol) in a 1:1:1 mixture of THF, methanol, water (4.5 mL) is added LiOH (0.09 g, 2.10 mmol). The reaction is stirred for 18 h at room temperature. The reaction is adjusted to pH 3 with 1N HCl and extracted with EtOAc to yield the title compound (0.12 g, 92%). LC-ES/MS m/e 602.0 (M−1).

Example 99

6-{4-[5-Cyclopropyl-3-(2,6-dichloro-phenyl)-3H-[1,2,3]triazol-4-ylmethoxy]-2-methyl-phenyl}-1-isopropyl-1H-indazole-3-carboxylic acid

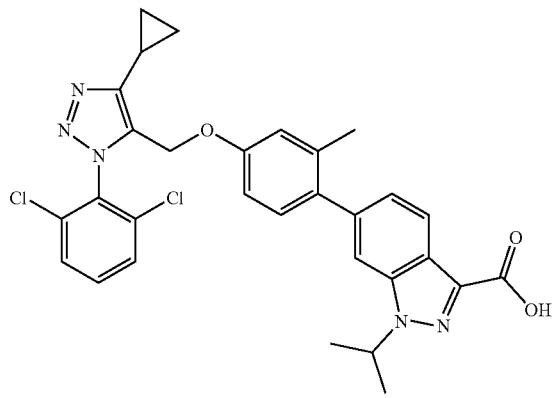

Step 1

6-{4-[5-Cyclopropyl-3-(2,6-dichloro-phenyl)-3H-[1,2,3]triazol-4-ylmethoxy]-2-methyl-phenyl}-1-isopropyl-1H-indazole-3-carboxylic acid methyl ester

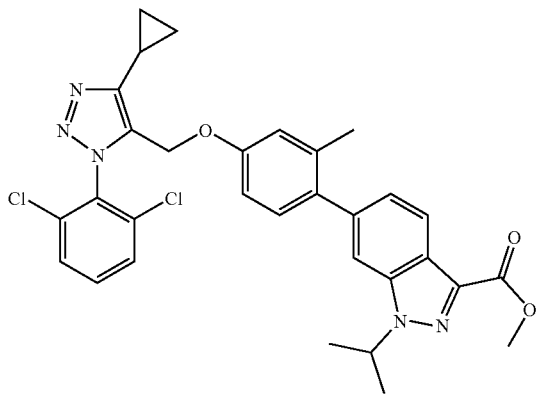

Nitrogen is bubbled through a solution of [5-cyclopropyl-3-(2,6-dichloro-phenyl)-3H-[1,2,3]triazol-4-yl]-methanol (0.23 g, 0.80 mmol) and 6-(4-hydroxy-2-methyl-phenyl)-1-isopropyl-1H-indazole-3-carboxylic acid methyl ester (0.2 g, 0.62 mmol) in toluene (10 mL) for 10 minutes. Tri-n-butyl phosphine (0.21 mL, 1.05 mmol) is added. Nitrogen is bubbled for an additional 10 min followed by addition of 1,1'-(azocarbonyl)-dipiperidine (0.27 g, 1.05 mmol). The reaction is stirred at room temperature for 18 h. The crude reaction is concentrated onto silica and chromatographed (40 g $SiO_2$, 0% to 40% EtOAc/Hexanes) to yield the title compound (0.11 g, 30%). LC-ES/MS m/e 590.0 (M+1).

Step 2

6-{4-[5-Cyclopropyl-3-(2,6-dichloro-phenyl)-3H-[1,2,3]triazol-4-ylmethoxy]-2-methyl-phenyl}-1-isopropyl-1H-indazole-3-carboxylic acid

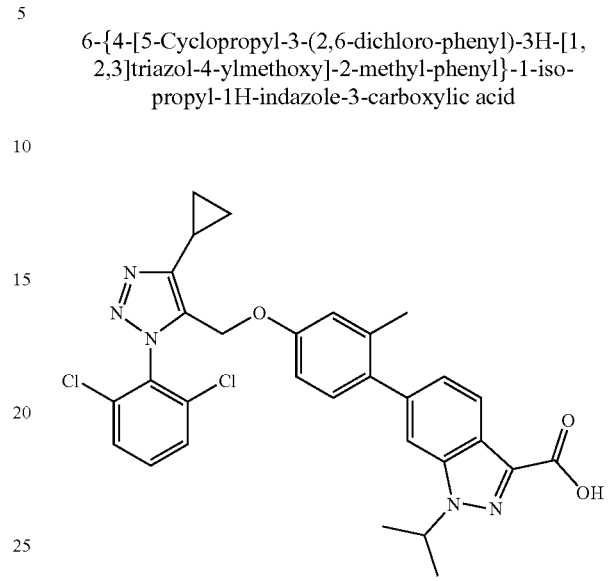

To a solution of 6-{4-[5-cyclopropyl-3-(2,6-dichloro-phenyl)-3H-[1,2,3]triazol-4-ylmethoxy]-2-methyl-phenyl}-1-isopropyl-1H-indazole-3-carboxylic acid methyl ester (0.18 g, 0.30 mmol) in a 1:1:1 mixture of THF, methanol, water (6.0 mL) is added LiOH (0.13 g, 3.0 mmol). The reaction is stirred for 18 h at room temperature. The reaction is adjusted to pH 3 with 1N HCl and extracted with EtOAc to yield the title compound (0.12 g, 70%). LC-ES/MS m/e 576.0 (M+1).

We claim:
1. A compound of

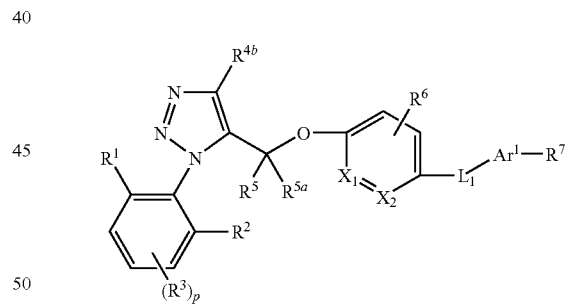

wherein p is 0, 1 or 2;

$X_1$ is C and $X_2$ is C;

$R^1$ and $R^2$ are independently selected from the group consisting of hydrogen, $C_1$-$C_3$ alkyl, $C_1$-$C_3$ haloalkyl, $C_1$-$C_3$ thiohaloalkyl, $C_1$-$C_3$ alkoxy, $C_1$-$C_3$ haloalkoxy, and halo;

$R^3$ is independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy, and halo;

$R^{4b}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;

$R^5$ and $R^{5a}$ are independently selected from the group consisting of hydrogen, and $C_1$-$C_3$ alkyl;

$R^6$ is selected from the group consisting of hydrogen, $C_1$-$C_3$ alkyl, $C_1$-$C_3$ haloalkyl, halo, and —$NO_2$;

$L_1$ is selected from the group consisting of a bond, $CR^a$=$CR^b$, ethynyl, $C_1$-$C_3$ alkyl-S—, $C_1$-$C_3$ alkyl-O—, $N(R^c)$—$C_1$-$C_3$ alkyl, and —$C_1$-$C_3$ alkyl-$N(R^c)$—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl, and $C_4$-$C_8$ alkylcycloalkyl;

$Ar^1$ phenyl, optionally substituted with one or two groups independently selected from the group consisting of hydroxy, $C_1$-$C_3$ alkyl, $C_1$-$C_3$ haloalkyl, halo, $C_2$-$C_4$ alkenyl, $C_2$-$C_4$ alkynyl, $C_1$-$C_4$ alkoxy, —$OC_1$-$C_2$ alkylphenyl, and $NHC(O)R^{10}$;

$R^7$ is selected from the group consisting of —COOH, —$C_1$-$C_3$ alkylCOOH, —O—$C_1$-$C_3$ alkylCOOH, —$C_3$-$C_8$ cycloalkylCOOH and, —$CONR^{11}R^{11}$;

each $R^{10}$ is independently selected from the group consisting of hydrogen, $C_1$-$C_3$ alkyl, and phenyl;

each $R^{11}$ is independently hydrogen, or $C_1$-$C_5$ alkyl; or a pharmaceutically acceptable salt thereof.

2. A compound according to claim 1 wherein p is 0 or 1;

$R^1$ and $R^2$ are independently selected from the group consisting of hydrogen, fluoro, chloro, $CF_3$, $SCF_3$, $OCF_3$;

$R^3$ is hydrogen, fluoro, chloro $C_1$-$C_3$ alkyl, $CF_3$, $SCF_3$, or $OCF_3$;

$R^{4b}$ is H, $C_1$-$C_3$ alkyl, $C_1$-$C_3$ haloalkyl, $C_1$-$C_3$ haloalkoxy, or $C_3$-$C_4$ cycloalkyl;

$R^5$ and $R^{5a}$ are each independently selected from H or $C_1$-$C_3$ alkyl;

$Ar^1$ group is phenyl, optionally substituted with one to two groups independently selected from $C_1$-$C_5$ alkyl, $C_1$-$C_3$ alkoxy, $C_1$-$C_2$ haloalkoxy, and $C_1$-$C_3$ haloalkyl;

$R^6$ is hydrogen, methyl, ethyl or chloro;

$L_1$ is a bond, ethenyl, —$CH(CH_3)$—S—, $C(CH_3)_2$—S—, —$CH_2O$—, —$CH_2CH_2O$—, —$CH(CH_3)$—O—, —$CH(CH_3)CH_2$—O—, —$CH(CH_2CH_3)$—O—, —$CH_2NH$—, —$CH_2CH_2NH$—, —$N(R^c)CH_2$—, $N(R^c)CH_2CH_2$—, or $N(R^c)CH_2CH_2CH_2$—; wherein $R^c$ is hydrogen, $C_1$-$C_2$ alkyl, benzyl or —$CH_2CH_2$—O—$CH_2$—;

$R^7$ is COOH, —$CH_2COOH$, —$CH(CH_3)COOH$, -cyclopropylCOOH, —$C(CH_3)_2COOH$, $CONH_2$, $C(O)NHCH_3$, or $C(O)NHCH_2CH_3$;

$R^{10}$ is hydrogen or $C_1$-$C_2$ alkyl; and $R^{11}$ is hydrogen or $C_1$-$C_2$ alkyl.

3. A compound according to claim 1, wherein p is 1; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl, acetylene, —$N(CH_3)CH_2$—, or —$N(CH_3)CH_2CH_2$—; $R^5$ and $R^{5a}$ are both hydrogen; $R^6$ is hydrogen, methyl, chloro or bromo; $Ar^1$ is phenyl, optionally substituted with a group selected from methyl, ethyl, propyl, isopropyl, cyclopropyl, methoxy, ethoxy, isopropoxy and cyclopropoxy; and $R^7$ is COOH.

4. A compound according to claim 1, wherein p is 1; $R^1$ and $R^2$ are independently selected from the group consisting of hydrogen, chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is a bond, —$N(CH_3)CH_2$—, or —$N(CH_3)CH_2CH_2$—; $R^5$ and $R^{5a}$ are both hydrogen; $R^6$ is hydrogen, methyl, ethyl or chloro; $Ar^1$ is phenyl optionally substituted with a group independently selected from methyl, ethyl, propyl, isopropyl, cyclopropyl, methoxy, ethoxy, isopropoxy and cyclopropoxy; and $R^7$ is COOH.

5. A compound according to claim 1, wherein p is 1; $R^1$ and $R^2$ are independently selected from the group consisting of hydrogen, chloro, fluoro, trifluoromethyl thiotrifluoromethyl, and trifluoromethoxy; $R^3$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl optionally substituted with a group selected from methyl, ethyl, propyl, isopropyl, cyclopropyl, methoxy, ethoxy, isopropoxy and cyclopropoxy; and $R^7$ is COOH.

6. A compound according to claim 1, wherein p is 1; $R^1$ and $R^2$ are independently selected from the group consisting of chloro, fluoro, trifluoromethyl, thiotrifluoromethyl, and trifluoromethoxy; $R^3$ is hydrogen; $R^{4b}$ is trifluoromethyl, isopropyl or cyclopropyl; $L_1$ is ethenyl; $R^5$ and $R^{5a}$ are both hydrogen; $R^6$ is hydrogen, methyl, ethyl or chloro; $Ar^1$ is phenyl, optionally substituted with a group selected from methyl, ethyl, propyl, isopropyl, cyclopropyl, methoxy, ethoxy, isopropoxy and cyclopropoxy; and $R^7$ is COOH.

7. A compound selected from the group consisting of:

4-[({4-[3-(2,6-dichlorophenyl)-5-trifluoromethyl-3H-[1,2,3]triazol-4-ylmethoxy]-2-methylphenyl}-methylamino)-methyl]-2-methyl-benzoic acid, 3-[({4-[3-(2,6-Dichloro-phenyl)-5-isopropyl-3H-[1,2,3]triazol-4-ylmethoxy]-2-methyl-phenyl}-methylamino)-methyl]-benzoic acid, 3-[({4-[5-Isopropyl-3-(2-trifluoromethoxy-phenyl)-3H-[1,2,3]triazol-4-ylmethoxy]-2-methyl-phenyl}-methylamino)-methyl]-benzoic acid, 4-[({4-[5-Isopropyl-3-(2,6-Dichloro-phenyl)-3H-[1,2,3]triazol-4-ylmethoxy]-2-methyl-phenyl}-methylamino)-methyl]-benzoic acid, 4-[({4-[5-Cyclopropyl-3-(2,6-dichloro-phenyl)-3H-[1,2,3]triazol-4-ylmethoxy]-2-methyl-phenyl}-methylamino)-methyl]-2-methyl-benzoic acid, 3-[({4-[3-(2-Chloro-6-fluoro-phenyl)-5-isopropyl-3H-[1,2,3]triazol-4-ylmethoxy]-2-methyl-phenyl}-methylamino)-methyl]-benzoic acid, or a pharmaceutically acceptable salt thereof.

8. The compound 4-[({4-[3-(2,6-dichlorophenyl)-5-trifluoromethyl-3H-[1,2,3]triazol-4-ylmethoxy]-2-methylphenyl}-methylamino)-methyl]-2-methyl-benzoic acid.

9. A pharmaceutical composition comprising a compound according to claim 1 and a carrier, diluent, or excipient.

* * * * *

UNITED STATES PATENT AND TRADEMARK OFFICE
CERTIFICATE OF CORRECTION

| | | |
|---|---|---|
| PATENT NO. | : 8,106,077 B2 | |
| APPLICATION NO. | : 12/298769 | |
| DATED | : January 31, 2012 | |
| INVENTOR(S) | : Michael Gregory Bell et al. | |

It is certified that error appears in the above-identified patent and that said Letters Patent is hereby corrected as shown below:

ON THE TITLE PAGE:

ADD: Item (60) "Related U.S. Application Data," please add the sentence --Provisional application No. 60/808,104, filed May 24, 2006 and Provisional application No. 60/870,001, filed December 14, 2006.--

Signed and Sealed this
Twenty-seventh Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,106,077 B2  Page 1 of 1
APPLICATION NO. : 12/298769
DATED : January 31, 2012
INVENTOR(S) : Michael Gregory Bell et al.

It is certified that error appears in the above-identified patent and that said Letters Patent is hereby corrected as shown below:

In the Claims:

Column 57, line 11, Claim 1, delete "$Ar^1$" and insert --$Ar^1$ is--, therefor.

Signed and Sealed this
Tenth Day of April, 2012

David J. Kappos
*Director of the United States Patent and Trademark Office*